(12) United States Patent
Skurkovich et al.

(10) Patent No.: US 6,863,890 B1
(45) Date of Patent: Mar. 8, 2005

(54) TREATMENT OF AIDS WITH ANTIBODIES TO GAMMA INTERFERON, ALPHA INTERFERON AND TNF-ALPHA

(75) Inventors: Boris Skurkovich, Pawtucket, RI (US); Simon V. Skurkovich, Rockville, MD (US)

(73) Assignee: Advanced Biotherapy, Inc., Woodland Hills, CA (US)

( * ) Notice: Subject to any disclaimer, the term of this patent is extended or adjusted under 35 U.S.C. 154(b) by 0 days.

(21) Appl. No.: 09/487,979

(22) Filed: Jan. 20, 2000

Related U.S. Application Data

(60) Division of application No. 09/306,286, filed on May 6, 1999, now abandoned, which is a continuation of application No. 08/995,730, filed on Dec. 22, 1997, now Pat. No. 6,333,032, which is a continuation of application No. 08/771,831, filed on Dec. 23, 1996, now Pat. No. 5,888,511, which is a continuation-in-part of application No. 08/025,408, filed on Feb. 26, 1993, now Pat. No. 5,626,843.

(51) Int. Cl.$^7$ .................. A61K 39/395; C07K 16/24
(52) U.S. Cl. ................ 424/158.1; 424/130.1; 424/141.1; 424/145.1; 530/387.1; 530/388.1; 530/388.23
(58) Field of Search ................ 424/130.1, 141.1, 424/133.1, 139.1, 145.1, 179.1; 530/387.1

(56) References Cited

U.S. PATENT DOCUMENTS

| 4,362,155 A | 12/1982 | Skurkovich et al. |
| 4,605,394 A | 8/1986 | Skurkovich et al. |
| 4,824,432 A | 4/1989 | Skurkovich et al. |
| 6,190,691 B1 * | 2/2001 | Mak |

FOREIGN PATENT DOCUMENTS

| WO | WO 92/16553 | 10/1992 |
| WO | 94/26307 | * 11/1994 |

OTHER PUBLICATIONS

Skolnick Trends In Biotech 18: 34–39 (2000).*
Lederman et al. Molecular Immunology 28: 1171–1181 (1991).*
Li et al. PNAS 77: 3211–3214 (1980).*
Skurkovich et al. Medical Hypotheses 42: 27–35 (1994).*
Merck Manual of Medical Information's (1997), pp. 1018–1019.*
Janeway et al Immunobiology 3rd Edition Garland Press NY 1997, Figure 7.31, p. 7:27.
Probert et al PNAS 92(24): 11294–8, 1995.
Abaza et al J. Protein Chem. 11(5):433–444, 1992.
Aderka et al., "Correlation between Serum Levels of Soluble Tumor Necrosis Factor Receptor and Disease Activity in Systemic Lupus Erythematosus," *Arthritis Rheum.* 36(8):1111–1120 (1993).

Altomonte et al., "Serum Levels of Interleukin–1b, Tumor Necrosis Factor–a and Interleukin–2 in Rheumatoid Arthritis, Correlation with Disease Activity." *Clin. Rheum.* 11(2):202–205 (1992).
Bevan et al., "Interferon Induced Parotitis and Epididymitis," *Lancet* 2:561 (1985).
Biglino et al., "Spontaneous Release of Interferon as a Predictor of Clinical Evolution in HIV–Positive Subjects," *Infection* 19(1):11/7–11/17 (1991).
Billard et al., "IFNα in Vivo Enhances Tumor Necrosis Factor Receptor Levels on Hairy Cells," *J. Immunol.* 145:1713–1718 (Sep. 1990).
Brahn et al., "Effects of Tumor Necrosis Factor Alpha (TNFα) on Collagen Arthritis," *Lymphokine and Cytokine Res.* 11(5):253–256 (1992).
Brennan et al., "TNFα–A Pivotal Role in Rheumatoid Arthritis," *Brit. J. Rheum.* 31(5):293–8 (1992).
Brod et al., "Interferon–$\beta_{1b}$ Treatment Deceases Tumor Necrosis Factor–α and Increases Interleukin–6 Production in Multiple Sclerosis," *Neurology* 46: 1633–1638 (Jun. 1996).
Burton, "Human Monoclonal Antibodies, Achievement and Potential," *Hospital Practice* 667–74 (Aug. 1992).
Carpenter et al., "The Pathogenesis of Autoimmunity in New Zealand Mice," *Lab Invest.* 23:628–634 (1970).
Chu et al., "Detection of Cytokines at the Cartilage/Pannus Junction in Patients with Rheumatoid Arthritis: Implications for the Role of Cytokines in Cartilage Destruction and Repair," *Brit. J. Rheum.* 31(10):653–661 (1992).
Chazerain et al., "Rheumatoid Arthritis–like Disease after Alpha–Interferon Therapy," *Ann. Intern. Med.* 116:427 (Mar. 1992).
Conlon et al., "Exacerbation of Symptoms of Autoimmune Disease in Patients Receiving Alpha–Interferon Therapy," *Cancer* 65:2237–2242 (1990).
Danis et al., "Circulating Cytokine Levels in Patients with Rheumatoid Arthritis: Results of a Double Blind Trial with Sulphasalazine," *Ann. Rheum. Disease* 51(8):946–950 (1992).

(List continued on next page.)

Primary Examiner—Phillip Gambel
(74) Attorney, Agent, or Firm—Morgan, Lewis & Bockius, LLP

(57) ABSTRACT

The present disclosure concerns the treatment of a patient with autoimmune disease, including AIDS, by neutralizing, removing or inhibiting different types of interferons, tumor necrosis factor, HLA class II antigens, IgE, and other pathological factors and/or their receptors, as well as neutralizing, removing or inhibiting autoantibodies, including antibodies to target cells, CD4 cells and DNA. Treatment comprises administration of an autoimmune inhibitor, or extracorporeal exposure of the patient's fluid to an immunosorbent comprising an autoimmune inhibitor, followed by return of the treated fluid to the patient; or it comprises a combined therapy involving extracorporeal immunosorption in conjunction with the administration of an autoimmune inhibitor.

2 Claims, No Drawings

OTHER PUBLICATIONS

Deleuran et al., "Localization of Tumor Necrosis Factor Receptors in the Synovial Tissue and Cartilage–Pannus Junction in Patients with Rheumatoid Arthritis," *Arthritis Rheum.* 35(10):1170–78 (1992).

DeStefano et al., "Acid–Labile Human Leukocyte Interferon in Homosexual Men with Karposi's Sarcoma and Lymphadenopathy," *J. Infec. Disease* 146:451–455 (1982).

Dorsett et al., "Anti–Lymphocyte Antibodies in Patients with the Acquired Immune Deficiency Syndrome," *Am. J. Med.* 78:621–626 (1985).

Elliott et. al., Treatment of Rheumatoid Arthritis with Chimeric Monoclonal Antibodies to TNF–α: Safety, Clinical Efficacy and Control of the Acute Phase Response, *J. Cellular Biochemistry. Suppl.* 17B:145 (1993).

Elliott et al., "Repeated Therapy with Monoclonal Antibody to Tumor Necrosis Factor α (cA2) in Patients with Rheumatoid Arthritis," *Lancet* 344:1125–1127 (1994).

Engleman et al., Treatment of NZB/NZW $F_1$ Hybrid Mice with *Mycobacterium bovis* Strain BCG or Type II Interferon Preparations Accelerates Autoimmune Disease, *Arthr. Rheum.* 24:1396–1402 (1981).

Fattovich et al., "Autoantibodies during Interferon–α Therapy for Chronic Hepatitis B," *Br. J. Med. Virol.* 34:132–135 (1991).

Feldman, et al., "Interferons and Autoimmunity," In *IFN 9*, Academic Press, p. 75 (1987).

Foulis et al., "Immunoreactive α–Interferon in Insulin–Secreting β Cells in Type I Diabetes Mellitus," *Lancet* 2:1423–1427 (1987).

Gendelman et al., "Induction of IFNα in Peripheral Blood Mononuclear Cells by HIV–Infected Monocytes," *J. Immunol.* 148:422–429 (1992).

Graninger et al., "Induction of Systemic Lupus erythematosus by Interferon–γ in a Patient with Rheumatoid Arthritis," *J. Rheumatol.* 18:1621–1622 (1981).

Gringeri et al., "Anti–Alpha Interferon Immunization Safety and Immunogenicity in Asymptomatic II HIV Positive Patients at High Risk of Disease Progression," *Cell. Mol. Biol.* 41(3):381–387 (1995).

Gringeri et al., "Absense of Clinical, Virological, and Immunological Signs of Progression in HIV–1–Infected Patients Receiving Active Anti–Interferon–α Immunization: A 30–Month Follow–Up Report," *J. Acquir. Immun. Defic. Syndr.* 13:55–67 (1996).

Heremans et al., "Interferon Treatment of NZB Mice Accelerated Progression of Autoimmune Disease," *Infect. Immun.* 21:925–930 (1978).

Hess et al., "Tumor Necrosis factor and Interferon as Prognostic Markers in Human Immunodeficiency Virus (HIV) Infection," *Infection 19. Suppl.* 2:S93–97 (1991).

Hirano et al., "Interleukin–6 and Its Relation to Inflammation and Disease," *Clin. Immunol.* 62:S60–S65 (1992).

Holt et al., "Cytokine Inter–Relationships and the Association with Disease Activity in Arthritis," *Brit J. Rheum.* 21(11):725–733 (1992).

Hooks et al., "Immune Interferon in the Circulation of Patients with Autoimmune Disease," *N. Eng. J. Med.* 301:5–8 (1979).

Johnson et al., "The Role of Antimyosin Antibodies in Acute Myocardial Infarction," *Sem. Nuc. Med.* 19:238 (1989).

Robert E. Walker et al., "Inhibition Of Immunoreactive Tumor Necrosis Factor–α by a Chimeric Antibody in Patients Infected with Human Immunodeficiency Virus Type 1", The Journal Of Infectious Diseases (1996) 174:63–8.

Stephen C Piscitelli et al., "Immune–Based Therapies For Treatment Of HIV Infection", The Annals of Pharmacotherapy (1996) Jan., vol. 30 pp. 62–76.

R. Le Naour et al., "Treatment of human monocyte–derived macrophages with a TNFα synthesis inhibtor prior to HIV1 infection: consequences on cytokine productin and viral replication," Res. Virol. (1994) 145, 199–207.

Larrey et al., "Exacerbation of Multiple Sclerosis after the Administration of Recombinant Human Interferon Alfa," *JAMA* 261:2065 (1989).

Lau et al., "Regulation of Tumor Necrosis Factor Receptor Expression by Acid–Labile Interferon–α from AIDS Sera," *AIDS Research and Human Retroviruses* 7:545–552 (1991).

Leinonen et al., "Circulating Immune Complexes Containing Chlamydial Lipopolysaccharide in Acute Myocardial Infarction," *Microbiol. Path.* 9:67–73 (1990).

Libikováet al., "Orbiviruses of the Kemerovo Complex and Neurological Disease," *Med. Microbiol. Immun.* 166:355–263 (1978).

Libikováet al., "Assay of Interferon and Viral Antibodies in the Cerebrospinal Fluid in Clinical Neurology and Psychiatry," *Acta. Biol. Med. Germ.* 38:879–893 (1979).

Link et al., "Increased Transforming Growth Factor–β, Interleukin–4, and Interferon–γ in Multiple Sclerosis," *Ann. Neurol.* 36:379–386 (1994).

Livden et al., "In Situ Localization of Interferons in Psoriatic Lesions," *Arch. Dermatol. Res.* 281(6):392–397 (1989).

Machold et al., "Interferon–γ Induced Exacerbation of Systemic Lupus Erythematosus," *J. Rheumat.* 17(6):831–832 (1990).

Matsuyama et al., "Cytocidal Effect of Tumor Necrosis Factor on Cells Chronically Infected with Human Immunodeficiency Virus (HIV): Enhancement of HIV Replication," *Proc. Natl. Acad. Sci. USA* 86:2365–2509 (1989).

Mauritz et al., "Treatment with Gamma–Interferon Trigger the Onset of Collagen Arthritis in Mice," *Arthritis & Rheumatism* 31:1297–1304 (1988).

Meijer et at., "Profiles of Cytokines (TNFα and IL–6) and Acute Phase Proteins (CRP and α IAG) Related to the Disease Course in Patients with Sustemic Lupus Erythematosus," *Lupus* 2:359–365 (1993).

Montalban et al., "Antiphospholipid Antibodies in Cerebral Ischemia," *Stroke* 22:750–753 (1991).

Murakami et al., "Diabetes Mellitus and Interferon–α Therapy," *Ann. Intern. Med.* 318 (Aug. 1995).

Ohta et al., Japanese *J. Gastroenterol.* 88:209–210 (1991).

Fernanda Grassi et al., "*Mycobacyerium avium* Complex Infectionj in Mice: Lack of Exacerbation after LP–BM5 Murine Leukemia Virus Infection", Infection And Immunity, vol. 64, No. 4, pp. 1203–1207 (Apr. 1996).

R.K. Cunnigham et al., "*Murine AIDS: A Model for the Human Disease or a Distinct Entity?*", Immunol Res. pp. 13:21–28 (1994).

Paniteh et al., "Exacerbations of Multiple Sclerosis in Patients Treated with Gamma Interferon," *Lancet* 1:893–894 (1987).

Preble et al., "Systemic Lupus Erythematosus: Presence in Human Serum of an Unusual Acid–Labile Leukocyte Interferon," *Science* 216:429–431 (1982).

Preble et al., "Serum Interferon in Patients with Psychosis," *Am. J. Psychiatry 142*(10):1184–1186 (1985).

Quesada et al., "Psoriasis and Alpha–Interferon," *Lancet* 2:1466–1468 (1986).

Quesada et al., "Clinical Toxicity of Interferons in Cancer Patients: A Review," *Clin. Oncol.* 2:234–243 (1986).

Remy et al., "Experimental Autoimmune Thyroiditis Induced by Recombinant Interferon–$\gamma$. ," *Immunol Today* 8:73 (1987).

Ronnblom, et al., "Possible Induction of Systemic Lupus Erythematosus by Interferon–$\alpha$ Treatment in a Patient with a Malignant Carcinoid Tumour," *J. Intern. Med.* 227:207–210 (1990).

Ronnblom et al., "Autoimmunity after Alpha–Interferon Therapy for Malignant Carcinoid Tumors," *Ann. Intern. Med. 115*:178–183 (1991).

Schattner et al., "Review: Interferons and Autoimmunity," *Am. J. Med. Sci. 295*.532–544 (1988).

Schilling et al., "Development of Systemic Lupus Erythematosus After Interferon Therapy for Chrome Myclogenous Leukemia," *Cancer 68*:1536–1534 (1991).

Sharriff et al., "Association between Tumor Necrosis Factor–$\alpha$ and Disease Progression in Patients with Multiple Sclerosis," *N. Eng. J. Med. 325*(7):467–472 (1992).

Shiozawa et al., "Interferon–Alpha in Lupus Psychosis," *Arthr. Rheum. 35*:417–422 (1992).

Sinha et al., "Autoimmune Diseases: The Failure of Self Tolerance," *Science 248*: 1380 (1990).

Skurkovich et al., "Immunosuppressive Effect of an Anti–Interferon Serum, " *Nature 217*:551-2 (1974).

Skurkovich et al., "The Probable Role of Interferon in Allergy," *Annals. of Allergy 35*:356–360 (1975).

Skurkovich et al., "Lymphocytes Cytotoxicity Towards Cells of Human Lumphoblastoid Lines in Patients with Rheumatoid Arthritis and Systemic Lupus Erythematosus," *Annals of Allergy 39*:344–350 (1977).

Skurkovich et al., "Interferon in the Serum of Autoimmune NZB/W and MRL/lpr/lpr Mice," *Annual International Congress for Interferon Research* (1981).

Skurkovich et al., "Aberrant IFN May Help HIV Survive and Replicate: Its Removal in AIDS Patients May Halt This Process and Help Restore the Immune System," *J. IFN Res. 12. Suppl. 1*:S110 (1992).

Skurkovich et al., "A Disturbance of Interferon Synthesis with the Hyperproduction of Unusual Kinds of Interferon Can Trigger Autoimmune Disease and Play a Pathogenic Role in AIDS: The Removal of These Interferons Can Be Therapeutic," *Med. Hypoth. 41*:177–185 (1993).

Skurkovich et al., (Revised) "A Disturbance of Interferon Synthesis with the Hyperproduction of Unusual Kinds of Interferon Can Trigger Autoimmune Disease and Play a Pathogenic Role in AIDS: The Removal of These Interferons Can Be Therapeutic." *Med. Hypoth. 42*:27–35 (1994).

Uehara et al., "Role of IFN–$\gamma$ in the Development of the Murine Acquired Immunodeficiency Syndrome, MAIDS," *J. Interferon Res. 13*, Suppl. 1: PW6–9 (Oct. 1993).

Vadhan–Raj et al., "Immunological Variables as Predictors of Prognosis in Patients with Karposi's Sarcoma and the Acquired Immunodeficiency Syndrome," *Cancer Res. 46*:417 (1986).

Van Snick et al., "Interleukin–6: An Overview," *Ann. Rev. Immunol. 8*:253–278 (1990).

Vento et al., "Rapid Decline of CD4+ Cells after IFN$\alpha$ Treatment in HIV–1 Infection," *Lancet 341*(Apr. 10, 1993).

Vileek et al., In *AIDS: The Epidemic of Karposi's Syndrome and Opportunistic Infections,* A.E. Friedman–Kien & L J. Laubenstein, eds. Masson Publishing, New York, New York, 1986.

Wood et al., "In Situ Hybridization of IL–6 in Rheumatoid Arthritis," *Clin. Exp. Immunol. 87*:183–189 (1992).

* cited by examiner

TREATMENT OF AIDS WITH ANTIBODIES TO GAMMA INTERFERON, ALPHA INTERFERON AND TNF-ALPHA

CROSS-REFERENCE TO RELATED APPLICATIONS

This application is divisional of U.S. application Ser. No. 09/306,286 filed on May 6, 1999, now abandoned, which is a continuation of U.S. application Ser. No. 08/995,730, filed on Dec. 22, 1997, now U.S. Pat. No. 6,333,032, which is a continuation of U.S. application Ser. No. 08/771,831, filed on Dec. 23, 1996, now U.S. Pat. No. 5,888,511 which is CIP of Ser. No. 08/025,408 filed Feb. 26, 1993 now U.S. Pat. No. 5,626,843.

FIELD OF INVENTION

The present invention is a method to treat autoimmune diseases and conditions in a patient, which are caused by the disturbance of the synthesis of interferons (IFNs) and certain other substances (e.g. tumor necrosis factors (TNFs)) and the production of autoantibodies to target cells, including CD4 cells, which damage the patient's immune system and have a direct pathological action on the patient's cells.

BACKGROUND OF THE INVENTION

The ability of the immune system to discriminate between "self" and "non-self" antigens is vital to the functioning of the immune system as a specific defense against invading microorganisms. "Non-self" antigens are those antigens on substances entering or in the body which are detectably different or foreign from the animal's own constituents, whereas "self" antigens are those which, in the healthy animal, are not delectably different or foreign from its own constituents. However, under certain conditions, including in certain disease states, an individual's immune system will identify its own constituents as "non-self," and initiate an immune response against "self" material, at times causing more damage or discomfort as from an invading microbe or foreign material, and often producing serious illness in an individual. Autoimmune disease results when an individual's immune system attacks his own organs or tissues, producing a clinical condition associated with the destruction of that tissue, as exemplified by diseases such as rheumatoid arthritis, insulin-dependent diabetes mellitus, acquired immunodeficiency syndrome ("AIDS"), hemolytic anemias, rheumatic fever, Crohn's disease, Guillain-Barre syndrome, psoriasis, thyroiditis, Graves' disease, myasthenia gravis, glomerulonephritis, autoimmune hepatitis, multiple sclerosis, systemic lupus erythematosus, etc. Blocking, neutralizing or inhibiting the immune response or removing its cause in these cases is, therefore, desirable.

Autoimmune disease may be the result of a genetic predisposition, alone or as the result of the influence of certain exogenous agents such as, viruses, bacteria, or chemical agents, or from the action of both. Some forms of autoimmunity arise as the result of trauma to an area usually not exposed to lymphocytes, such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of the individual to antigens which are antigenically similar to, that is cross-reactive with, the individual's own tissue. For example, in rheumatic fever an antigen of the streptococcal bacterium, which causes rheumatic fever, is cross-reactive with parts of the human heart. The antibodies cannot differentiate between the bacterial antigens and the heart muscle antigens, consequently cells with either of those antigens can be destroyed.

Other autoimmune diseases, for example, insulin-dependent diabetes mellitus (involving the destruction of the insulin producing beta-cells of the islets of Langerhans), multiple sclerosis (involving the destruction of the conducting fibers of the nervous system) and rheumatoid arthritis (involving the destruction of the joint lining tissue), are characterized as being the result of a mostly cell-mediated autoimmune response and appear to be due primarily to the action of T-cells (See, Sinha et al., Science 248: 1380 (1990)). Yet others, such as myesthenia gravis and systemic lupus erythematosus, are characterized as being the result of primarily a humoral autoimmune response (Id.). Nevertheless, the autoimmune diseases share a common underlying pathogenesis, resulting in the need for safe and effective therapy. Yet none of the presently available drugs are completely effective for the treatment of autoimmune disease, and most are limited by severe toxicity.

In recent years, a new point of view on the pathogenesis of autoimmune diseases, including AIDS, has developed, in which it has been suggested that autoimmune disease is connected with a disturbance in the synthesis of interferons and other cytokines induced by interferons (Skurkovich et al., Nature 217:551–2 (1974); Skurkovich et al., Annuals of Allergy 35:356 (1975); Skurkovich et al., J. IFN Res. 12, Suppl. 1:S110 (1992); Skurkovich et al. Med. Hypoth. 41:177–185 (1993); Skurkovich et al., Med. Hypoth. 42:27–35 (1994); Gringeri et al., Cell. Mol. Biol 41(3):381–387 (1995); Gringeri et al. J Acquir. Immun. Defic. Syndr. 13:55–67 (1996)). IFN has been found in the circulation of patients with autoimmune diseases, and it has been neutralized in vivo with antibody to leukocyte (alpha) IFN ("IFNα"). Healthy people do not have interferon in their blood (Skurkovich et al., 1975). In addition, it has been shown that hyperproduced IFNα is found not only in the circulation of patients with classic autoimmune diseases, but also in patients with HIV infection (DeStefano et al., J. Infec. Disease 146:451 (1982)), where its presence is a predictive marker of AIDS progression (Vadhan-Raj et al., Cancer Res. 46:417 (1986)). The IFN induced by HIV has low anti-(HIV) viral activity (Gendelman et al.,J. Immunol. 148:422 (1992)). It was shown that the circulating IFNα possesses antigenic specificity like natural IFNα, which is pH stable, but this interferon is pH labile like IFNγ (Preble et al., Science 216:429 (1982)); thus, it is known as aberrant IFNα.

Investigators have also shown that tumor necrosis factors (TNFα and TNFβ) also play a significant role in the pathology of autoimmune diseases. For example, the presence of TNFα has been correlated with rheumatoid arthritis (RA) (Brennan et al., Brit. J. Rheum. 31(5):293–8 (1992)), and TNFα has been found to be related to an increase in the severity of collagen induced arthritis in animal models (Brahn et al., Lymphokine and Cytokine Res. 11(5):253 (1992)), while it has also been shown that anti-TNF alpha antibody administration ameliorates collagen induced arthritis (Williams et al. Clin. & Exp. Immunol 87(2):183 (1992)). TNFα is increased in the serum of PA patients (Holt et al. Brit. J. Rheum. 21(11):725 (1992); Altomonte et al., Clin. Rheum. 11(2):202 (1992), and both the cytokine (Chu et. al., Brit. J. Rheum. 31(10):653–661 (1992)) and its receptors have been identified in rheumatoid synovium, as well as at the cartilage-pannus junction (Deleuran et al., Arthritis Rheum. 35(10)1180 (1992)).

In addition, increased circulating levels of TNFα have been found to be associated with disease progression in patients with multiple sclerosis (Shariff et at., N. *Engl. J. Med.* 325(7):467–472 (1992)); while increased serum levels of soluble TNF receptor and interferon γ ("INFγ") have been independently correlated with disease activity in individuals, e.g., those with systemic lupus erythematosus (Aderka et. al., *Arthritis Rheum.* 36(8): 1111–1120 (1993); Machold et al., *J. Rheumat.* 17(6):831–832 (1990)). The spontaneous release of interferon and TNF in HIV-positive subjects (Vilcek et al., In *AIDS: The Epidemic of Karposi's Syndrome and Opportunistic Infections*, A. E. Friedman-Kien & L. J. Laubenstein, eds. Masson Publishing, New York, N.Y., 1986; Hess et al., *Infection* 19, Suppl 2:S93–97 (1991); Biglino et al., *Infection* 19 (1):11/7–11/7 (1991)), and the decline seen in the serum levels of TNF-α in RA patients following long term administration of the disease modifying drug sulfasalazine (Danis et al., *Ann. Rheum. Disease* 51(8) :946 (1992)), further suggest that the concentrations of cytokines and/or their receptors is reflected in the clinical course of autoimmune disease.

IFN is known to induce tumor necrosis factor (TNF) and its receptors (Lau et al. AIDS Research and Human Retroviruses 7:545 (1991)), which enhances virus replication (Matsuyama et al., *Proc. Natl. Acad. Sci. USA* 86:2365 (1989)). In addition to its presence in the circulation, IFNs have also been found in the cerebrospinal fluid in some patients with psychiatric mid neurologic diseases (Lebikoa et al., *Acta. Biot Med Germ.* 38:879 (1979); Preble et al, *Am. J. Psychiatry*, 142:10 (1985)), as well as in patients with rheumatoid arthritis. Therefore, since healthy people do not have interferons in their spinal or synovial fluids, the inventors have suggested that one or more alpha IFNs may be involved in the development of the initial autoimmune disease response. Consequently, the removal and/or neutralization of IFNα has been proposed as a method of treatment of patients with autoimmune disease, including AIDS. The appearance of cytokines and autoimmunogens induced by IFNα and their prolonged circulation in the body is an inseparable part of the development of autoimmune disease, triggering immune dysregulation in autoimmune disease, including AIDS. See, U.S. Pat. Nos. 4,824,432; 4,605,394; and 4,362,155, herein incorporated by reference. However, it now appears that gamma IFN ("IFNγ") can also play a pathogenetic role since each participates in immune regulation.

In addition to classic autoimmune disease and AIDS, autoantibodies play a pathogenic role in many other pathological conditions. For example, after cell (or organ) transplantation or after heart attack or stroke, certain antigens from the transplanted cells (organs) or necrotic cells from the heart or the brain can stimulate the production of autoantibodies or immune lymphocytes (Johnson et al., *Sem. Nuc. Med.* 19:238 (1989); Leinonen el al., *Microbiol. Path.* 9:67 (1990); Montalban et al., *Stroke* 22:750 (1991)), which later participate in rejection (in the case of a transplant) or attack cardiac or brain target cells, aggravating the condition. Moreover, in human autoimmune disease certain cells express abnormally elevated levels of HLA class II antigens, which is stimulated by the disturbed production of cytokines, e.g., IFNγ alone, or IFNγ in combination with TNF (Feldman et al. "Interferons and Autoimmunity," In IFN 9, Academic Press, p. 75 (1987).

Recognition of the important role of cytokines in autoimmune disease has fostered the development of a new generation of therapeutic agents to modulate cytokine activity. Preliminary results of trials in which anti-interferon polyclonal antibodies were administered to a small group of rheumatoid patients suggest improvement in both the clinical and the laboratory manifestations of the disease (Skurkovich et al., *Annals of Allergy* 39:344–350 (1977)). Moreover, proteins, such as polyclonal antibodies and soluble receptors targeted against interferons and TNF-α are currently being evaluated in clinical trials for the treatment of RA and other autoimmune diseases. The administration of monoclonal antibodies to TNF-α has provided encouraging early results in the treatment of patients with severe RA (Elliott et. al., *J. Cell. Biochem., Suppl* 17B: 145 (1993); Elliott et al., *Lancet* 344: 1105–1110 (1994)). Also positive preliminary results were achieved in AIDS patients given antibodies or other agents to reduce the level of circulating IFNα in the body (Skurkovich et al., 1994; Gringeri et al. 1996). However, because autoimmune diseases are complex, often characterized by multiple cytokine abnormalities, effective treatment appears to require the simultaneous administration or utilization of several agents, each targeting a specific cytokine pathway or its by-product. To meet this need, the methods of treatment of the present invention include not only the use of specific antibodies, but also, provide pleiotrophic autoimmune inhibitors, including antibodies to cytokines and HLA class II antigens, and antigens for the removal of autoantibodies to target cells or DNA. The use of these antibodies and antigens as disclosed in the present invention results in the removal, neutralization or inhibition of the pathogenic cytokine(s), HLA class II antigens, and/or autoantibody(ies) to target cells or DNA from the autoimmune patient, thereby significantly improving the quality of life of the individual.

SUMMARY OF THE INVENTION

The present invention concerns the treatment of autoimmune diseases, including AIDS, by blocking, inhibiting, neutralizing, or removing harmful interferons, tumor necrosis factors, and other pathological immunogens or factors, or their receptors, and antibodies to target cells, including CD4 cells, in a patient in need of such treatment.

It is an object of the present invention to provide a method of treating autoimmune disease in a patient comprising administering to the patient an effective amount of anti-IFNγ antibodies and/or antibodies to IFNγ receptor.

In addition, it is an object of the invention to provide a method of treating autoimmune disease in a patient comprising administering to the patient an effective amount of a plurality of at least two antibodies selected from the group consisting of anti-IFNα antibodies and antibodies to IFNα receptor, anti-IFNγ antibodies and antibodies to IFNγ receptor, anti-TNF antibodies and antibodies to TNF receptor, and antibodies to an HLA class II antigen or its receptor. In particular, it is an object of the invention to provide a method of treating autoimmune disease, wherein a plurality of antibodies is administered comprising (a) at least one anti-IFNα antibody and/or antibody to IFNα receptor, and (b) at least one anti-IFNγ antibody and/or antibody to IFNγ receptor. It is also a particular object of the invention to provide a method of treating autoimmune disease, wherein at least one anti-TNF antibody and/or antibody to TNF receptor is administered, alone or in conjunction with one or more of the following: anti-IFNα antibody, antibody to IFNα receptor, anti-IFNγ antibody and/or antibody to IFNγ receptor. It is further a particular object of the invention to provide a method of treating autoimmune disease, wherein at least one antibody to an HLA class II antigen and/or its receptor is administered, alone or in conjunction with one or more of the following:

anti-IFNα antibody, antibody to IFNα receptor, anti-IFNγ antibody, antibody to IFNγ receptor, anti-TNF antibody and/or antibody to TNF receptor.

It is also an object of the invention to provide a method of treating autoimmune disease in a patient comprising, in conjunction with administering to the patient an effective amount of a plurality of at least two antibodies selected from the group consisting of anti-IFNγ antibodies and antibodies to IFNα receptor, anti-IFNγ antibodies and antibodies to IFNγ receptor, anti-TNF antibodies and antibodies to TNF receptor, and antibodies to an HLA class II antigen or its receptor, an extracorporeal treatment comprising removing antigens from the patient by drawing fluid from the patient; passing said fluid through an immunosorbent comprising a combination of at least two antibodies selected from the same group; followed by returning the treated fluid to the patient. In particular, it is an object of the invention to provide a method of treating autoimmune disease, wherein the extracorporeal treatment comprises passing the patient's fluid through an immunosorbent comprising a combination of at least two antibodies selected from (a) at least one anti-IFNα antibody and/or antibody to IFNα receptor, and (b) at least one anti-IFNγ antibody and/or antibody to IFNγ receptor. It is also a particular object of the invention to provide an extracorporeal method of treatment, wherein the immunosorbent comprises at least one anti-TNF antibody and/or antibody to TNF receptor, alone or in conjunction with one or more of the following: anti-IFNα antibody, antibody to IFNα receptor, anti-IFNγ antibody and/or antibody to IFNγ receptor. It is further a particular object of the invention to provide an extracorporeal treatment, wherein the immunosorbent comprises at least one antibody to an HLA class II antigen and/or its receptor, alone or in conjunction with one or more of the following: anti-TFNα antibody, antibody to IFNα receptor, anti-IFNγ antibody, antibody to IFNγ receptor, anti-TNF antibody and/or antibody to TNF receptor.

Yet another object of the invention is to treat specific autoimmune diseases by the administration of autoimmune inhibitor to the patient. For example, a method of treatment is provided comprising administering to the patient an effective amount of beta interferon in addition to one or more antibodies selected from the group consisting of anti-IFNα antibody and antibodies to IFNα receptor, anti-IFNγ antibodies and antibodies to IFNγ receptor, anti-TNF antibodies and antibodies to TNF receptor, and antibodies to an HLA class II antigen or its receptor. This method is particularly effective for the treatment of multiple sclerosis. An additional method of treatment is provided comprising administering to the patient an effective amount of antibodies to interleukin ("IL"), preferably to IL-6, in addition to one or more antibodies selected from the group consisting of anti-IFNα antibodies and antibodies to IFNα receptor, anti-IFNγ antibodies and antibodies to IFNγ receptor, anti-TNF antibodies and antibodies to TNF receptor, and antibodies to an HLA class II antigen or its receptor. This method is particularly effective for the treatment of systemic lupus erythematosus and insulin-dependent diabetes mellitus.

It is also an object of the invention to provide a method of treating specific autoimmune diseases by the extracorporeal exposure of the patient's fluid to an immunosorbent comprising autoimmune inhibitor, followed by the return of the treated fluid to the patient. This method may be practiced alone, or in conjunction with the administration of autoimmune inhibitor to the patient. For example, a method of treatment is provided comprising exposing the patient's fluid to an immunosorbent comprising an effective amount of antibodies to interleukin, preferably anti-IL-6 antibody, in addition to one or more antibodies selected from the group consisting of anti-IFNα antibody and antibodies to IFNα receptor, anti-IFNγ antibodies and antibodies to IFNγ receptor, anti-TNF antibodies and antibodies to TNF receptor, and antibodies to an HLA class II antigen or its receptor. This method is particularly effective for the treatment of systemic lupus erythematosus and insulin-dependent diabetes mellitus.

It is a further particular object of the invention to provide a method of treating specific autoimmune diseases, wherein the specific extracorporeal treatment comprises passing the patient's fluid through an immunosorbent comprising antibody (ies) to immunoglobulin E ("IgE"), followed by the return of the treated fluid to the patient. This method may be practiced alone, or in conjunction with the administration of autoimmune inhibitor. For example, for treating certain diseases related to hypersensitivity of the immediate type, e.g., bronchial asthma, antibody to IgE is used as an immunosorbent, alone or in conjunction with other autoimmune inhibitors, such as antibodies to IFNs and/or to TNF or to their receptors.

It is a further object of the invention to provide a method of treating autoimmune disease in a patient comprising, alone or in conjunction with administering to the patient an effective amount of one or more antibodies (e.g., anti-IFNα antibodies, antibodies to IFNα receptor, anti-IFNγ antibodies, antibodies to IFNγ receptor, anti-TNF antibodies, antibodies to TNF receptor, and antibodies to an HLA class II antigen or its receptor), extracorporeal treatment comprising removing autoantibodies from the patient by drawing fluid from the patient; passing said fluid over anti-TNF antibodies comprising an effective amount of different target cells, CD4 cells and/or DNA, to remove, neutralize or inhibit auto-antibodies in the patient's fluid; followed by returning the treated fluid to the patient. The immunosorbent for extracorporeal treatment may further comprise one or more antibodies (e.g., anti-IFNα antibodies, antibodies to IFNα receptor, anti-IFNγ antibodies, antibodies to IFNγ receptor, anti-TNF antibodies, antibodies to TNF receptor, and antibodies to an HLA class II antigen or its receptor.

In particular, it is an object of the invention to provide a method of treating specific autoimmune diseases, wherein the specific extracorporeal treatment comprises passing the patient's fluid through an immunosorbent comprising target cells. For example, for the treatment of rheumatoid arthritis, target cell antigens from joints, skin, collagen, and possibly other target antigens are used as immunosorbents, alone or in conjunction with other autoimmune inhibitors, such as antibodies to IFNs and/or antibodies to TNF or their receptors and/or antibodies to HLA class II antigens or their receptors. In addition, for the treatment of rheumatic fever, the invention provides an immunosorbent comprising antibodies to IFNs and/or to TNF and/or their receptors and/or to HLA class II antigens and/or their receptors and/or other substances, in conjunction with a second cardiac tissue sorbent for removing autoantibodies against cardiac tissue. The second sorbent can also include selected serotypes of *Streptococcus* (group "A"), because certain antigens from cardiac tissue and some serotypes of *Streptococcus* are antigenically similar. For the treatment of autoimmune diseases of the central nervous system, target cell antigens from the brain cells are used to absorb autoantibodies formed against brain cells.

It is also a particular object of the invention to provide a method of treating specific autoimmune diseases, wherein the specific extracorporeal treatment comprises passing the patient's fluid through an immunosorbent comprising DNA. For example, for the treatment of systemic lupus erythematosus the immunosorbent comprises DNA to remove, reduce or neutralize the patient's anti-DNA autoantibodies.

Yet another particular object of the invention to provide a method of treating specific autoimmune diseases, wherein the specific extracorporeal treatment comprises passing the patient's fluid anti-TNF antibodies comprising CD4 cells. For example, for the treatment of AIDS, the immunosorbent comprises CD4 cells, alone or in conjunction with other autoimmune inhibitors, such as antibodies to IFNs and/or TNF and/or HLA class II antigen, or their receptors.

It is also an object of the invention to provide pharmaceutical compositions comprising in combination an effective amount to treat a patient with autoimmune disease of a plurality of two or more components selected from the group consisting of: anti-IFNα antibodies, antibodies to IFNα receptor, anti-IFNγ antibodies, antibodies to IFNγ receptor, anti-TNF antibodies, antibodies to TNF receptor, and antibodies to an HLA class II antigen or its receptor, and a pharmaceutically acceptable carrier therefor.

It is a further object of the invention to provide kits or compositions comprising an immunosorbent comprising an effective amount to extracorporeally remove, reduce or neutralize one or more autoimmunogens from the fluid of a patient with autoimmune disease of at least one of the following antibodies: anti-IFNα antibodies, antibodies to IFNα receptor, anti-IFNγ antibodies, antibodies to IFNγ receptor, anti-TNF antibodies, antibodies to TNF receptor, antibodies to an HLA class II antigen or to its receptor, antibodies to IgE. While it is yet another object to provide kits or compositions comprising an immunosorbent comprising an effective amount to extracorporeally remove, reduce or neutralize one or more auto-antibodies from the fluid of a patient with autoimmune disease of at least one of the following: target cells, CD4 cells, and DNA.

Additional objects, advantages and novel features of the invention will be set forth in part in the description which follows, and in part will become apparent to those skilled in the art on examination of the following, or may be learned by practice of the invention.

DESCRIPTION OF PREFERRED EMBODIMENTS

The present invention provides methods for treating various autoimmune diseases, including AIDS by blocking, neutralizing or inhibiting different kinds of interferons, tumor necrosis factor, HLA class II antigens, and other pathological factors, which are common in most autoimmune disease, and which participate in damage of the immune system and the development of autoimmune disease. In addition, it provides methods for removing, reducing or neutralizing antibodies which may destroy the DNA or target cells of autoimmune disease patients and/or the CD4 cells in patients with AIDS.

Interferon is now known to be not only an antiviral and anti-proliferative cytokine, but it is also a factor which plays an important role in normal and pathological immunity. For the normal functioning of the immune system, it is necessary for an individual to have a normally functioning cytokine system. The interferon system in humans is a very stable system. Since healthy people do not have interferon in their blood, prolonged hyperproduction of interferon—primarily alpha but sometimes gamma interferons—typically indicates the presence of immune disease.

Upon observation of the diverse clinical pictures manifested in patients with various autoimmune diseases, which includes hypersensitivity of the immediate type (e.g., bronchial asthma, which is also an autoimmune condition), and AIDS (a viral disease with autoimmune components), it becomes apparent that these diseases have in common a large number of similar laboratory characteristics. This suggests that a similar disease mechanism is occurring in each autoimmune disease, but in different target cells. Thus, it is the unique target (e.g., skin, joints, liver, and the like) of each autoimmune disease that leads to its characterization in terms of clinical manifestations. For example, an autoimmune attack destroying the insulin producing beta-cells of the islets of Langerhans of an individual would be diagnosed as diabetes (Type I), whereas autoimmune destruction of the conducting fibers of the nervous system is characteristic of multiple sclerosis, or autoimmune destruction of the joint lining tissue is characteristic of rheumatoid arthritis. Likewise in the case of skin transplantation, the skin area can be damaged. Yet in each case, the mechanism underlying the autoimmune response is similar; a high level of IFNs, a detectable level of TNF, an elevated level of HLA class II antigens in the blood or on the surface of the cells, and antibodies to target cells. In addition, cells taken from autoimmune patients show a decreased production of IFNs in vitro, even after stimulation with an interferonogen. Consequently, the method of treatment of the various autoimmune diseases is similar in principle, despite the apparent clinical differences among the diseases.

The present invention is based upon the inventors' conclusions that the optimal treatment of each different autoimmune disease or autoimmune condition involves the removal, neutralization or inhibition of complex pathological agents (including hyperproduced cytokines) from the patient, and/or the administration to the patient of an effective amount of selected molecules or antibodies, or their receptors, to bind to, neutralize or inhibit the circulating pathological agents and/or those on the surface of the cells targeted in the specific autoimmune response ("target cells"). The primary indicator of each autoimmune disease is the hyperproduction of IFNα or, to be more exact, the disturbance of the synthesis of one or more alpha IFNs (IFNα comprises at least 15 distinct subtypes). In most patients with autoimmune disease, some level of IFNγ is also found. Patients with systemic lupus erythematosus ("SLE") and AIDS appear to have the highest levels of IFNα, as compared with patients with other autoimmune diseases (See, Skurkovich et al., *Annals of Allergy* 35:356 (1975); DeStefano et al., 1982).

IFNα is secreted by somatic cell and leukocytes, accumulating on the membranes of cells and entering the bloodstream. In autopsies, IFNα has been found, for example, on the surface of cells in the pancreas of patients with insulin dependent diabetes (Foulis et. al, *Lancet* 2:1423 (1987)), in skin lesions of patients with psoriasis (Livden et. al., *Arch Dermatol. Res.* 281 :392 (1989)), on the surface of brain cells of patients with the psychiatric complications of systemic lupus erythematosus ("SLE") ((Shiozawa et al., *Arthr. Rheum.* 35:417 (1992)), and in the circulating body fluids of animal and human patients with autoimmune disease ((Skurkovich et al. 1975; DeStefano et al. 1982). For instance, IFNα has been found circulating in the blood of autoimmune NZB/W and mrl/lpr mice (Skurkovich et al. *Ann. Internat'l Congress for Interferon Research* (1981), and in the circulation of patients with RA, SLE, Sjogren's syndrome, scleroderma, insulin-dependent diabetes, bronchial asthma, AIDS, and other autoimmune diseases (Skurkovich et. al., 1975; Hooks et al., *N Engl J. Med* 301:5 (1979); DeStefano et al. 1982). Of particular interest, is a recent discovery that interferon is also found in the blood and spinal fluid of patients with neurological diseases, including, e.g., schizophrenia (Lebikova et al., *Med Microbiol Immun.* 166:355 (1978); Preble et al., 1985), depression, and multiple sclerosis (Link et al., *Ann. Neurol.* 36:379 (1994)).

The uninterrupted production of IFNα is apparently connected with the weakening or absence of the IFNα repressor. In general, hyperproduction of IFNα is an indicator of immunological disintegration, and many scientists consider IFNα to be a recognized marker of the presence of an autoimmune condition ((Skurkovich et al., 1975; Hooks el ail. 1979). Moreover, the disturbance of IFNα production in an individual changes the biological activity of the cells, bringing about the production of autoantigens (Skurkovich et al., 1994; Shattner et al. *Am. J. Med. Sci.* 295:532 (1988)). The hyperproduction of IFNα also stimulates the production of tumor necrosis factor and its receptors, particularly TNFα (Lau et al., 1991). Increased production of autoantigens leads to the activation of the T-cells, and to the production of IFNγ. It is possible every autoantigen stimulates the induction of a unique, specific IFNγ.

In addition, in human autoimmune disease some cells express abnormally elevated levels of HLA class II antigens, or in some cases HLA class I or III antigens, which is stimulated by the disturbed production of IFNγ, alone or in combination with TNF (Feldman et. al., 1987). This synthesis of HLA class II antigens (or HLA class I or III antigens) plays an important role in the pathogenesis of autoimmune disease and AIDS. The disturbance of the production of HLA class II antigen in an individual leads to a pathological disturbance of the presentation of antigens to the T-cells, to disrupted T/B cooperation, and to the dysregulation of the interactions among T-cells.

Every antigen is an interferonogen; "self" cannot induce IFN. Thus, the production of IFN signals the invasion by a foreign antigen, or in this case the presence of an autoantigen. The production of IFN and its prolonged circulation in the body is an inseparable part of the development of autoimmune disease, and triggers immunological chaos. For example, antibodies to CD4 in patients with HIV infection (Dorsett et al. *Am. J. Med.* 78:621 (1985)) can cross-react with HLA class II antigen, which in turn are induced by IFNγ, or by IFNγ in combination with TNF, and possibly by IFNα, which induces TNF. IFNα and IFNγ are biologically dangerous elements in certain people. If injected into a human or animal with a genetic predisposition to develop an autoimmune disease, the interferons can trigger or exacerbate the autoimmune disease in the recipient. For example, administration of IFNα, IFNγ, or an inducer of IFNα to autoimmune NZB/W and MRL/lpr/lpr mice have resulted in an aggravation of the autoimmune response in the animal, augmented morbidity, and increased mortality (Carpenter et al. *Lab Invest.* 23:628 (1970); Engleman et al. *Arthr. Rheum.* 24:1396 (1981); Heremans et al. *Infect. Immun.* 21 :925 (1978)). Injection of one unit of r-IFNγ into the thyroid gland of CBA mice caused autoimmune thyroiditis (Remy et al. *Immunol Today* 8:73 (1987)). Administration of IFNα to human patients with psoriasis (a disease with an autoimmune component) was found to exacerbate, rather than alleviate the clinical manifestations of the disease (Quesada et al., *Lancet* 2:1466 (1986)). Injection of natural or recombinant IFNα ("r-IFNα"), and sometimes IFNγ, to cancer patients has reportedly triggered or exacerbated autoimmune parotitis, epididymitis, and thyroiditis, SLE, RA, Graves' disease, and other autoimmune conditions (See, e.g., Quesada et al., *Clin. Oncol.* 2:4234 (1986); Bevan et al. *Lancet* 2:561 (1985); Ronnblom, et al. *J Intern. Med* 227:207 (1990); Conlon et al., *Cancer* 65:2237 (1990); Machold et al.,*J Rheum.* 17:831 (1990); Schilling et al., *Cancer* 68:1536 (1991); Ronnblom et al., *Ann. Intern. Med* 115:178 (1991)). IFNα injections in patients with different types of viral hepatitis have induced autoimmune hepatitis (See, e.g., Ohta et al. *J Gastroenterol.* 88:209 (1991); Fattovich et al., *Brit. J. Med. Virol.* 34: 132 (1991)). In addition, it has been reported that a patient with multiple sclerosis ("MS") given r-IFNα subcutaneously (Larrey et al., *JAMA* 261:2065 (1989)), and another given r-IFNγ (Paniteh et al., *Lancet* 1:893 (1987)) intrathecally, manifested clinical relapses at rates significantly higher than expected.

On the other hand, the neutralization of individual cytokines, such as INFα or TNFα, from the blood has been associated with a significant therapeutic effect, in patients with RA and in patients with AIDS (Skurkovich et. al. 1975; Gringeri et al., 1996). Thus, it is a purpose of the present invention to provide methods of treating autoimmune disease by the use of pleiotrophic autoimmune inhibitors, acting on each of the known aberrant cytokine pathways in the patient and/or removing pathogenic cytokines, HLA antigens, or autoantibodies from the autoimmune patient.

The terms "patient" and "individual" are interchangeably used to mean a warm-blooded animal, such as a mammal, suffering from a disease, such as an autoimmune disease or "graft versus host" disease, or is in danger of rejection of a transplanted allogeneic tissue or organ. It is understood that humans and animals are included within the scope of the term "patient" or "individual."

"Cytokines" are intercellular mediators secreted by the lymphocytes and/or macrophages. For example, cytokines play a role in the generation of an immune response, such as in an immune response to an infection or infectious organism. Cytokines including, for example, interferens (IFNα and IFNγ) and TNFs induce other cytokines which participate in the development of different autoimmune conditions and diseases. In the development of anti-cytokine therapy in accordance with the present invention, considerable emphasis has been placed on these three cytokines, because it appears that by neutralizing these key cytokines (IFNα, IFNγ and TNF), it is possible to decrease, halt or prevent the synthesis of the cytokines induced by them. However, is certain autoimmune conditions or diseases, including IDDM and SLE, the induction of another cytokine (interleukins, specifically IL-6) is so great and exerts such a strong pathological influence, that it is desirable to remove IL-6 together with the other cytokines.

IL-6 is made by several cells; including T-cells, B-cells, and others (Hirano et al., *Clin. Immunol* 62:S60 (1992)), and induces insulinitis in IDDM. In response to IFNγ and TNF, B-cells of the pancreas produce large quantities of IL-6. It is also an important pathological factor in the pathogenesis of SLE, where is has been found to be present at a high level. IL-6 stimulates differentiation in B-cells and hyperactivity of T-cells (Snick et al., *Ann. Rev. Immunol* 8:253 (1990)). The increase in IL-6 parallels the increase of TNFα (Majer et. al., *Lupus* 2:359–365 (1993)).

The term "autoimmune inhibitor" is used to refer to a "compound" or "compounds," including one or more molecules, antigens, and/or antibodies (alone or in combination), which when administered in an effective amount to a patient, binds to, neutralizes or inhibits circulating pathological agents and/or those on the surface of target cells, and which when placed in extracorporeal contact with the patient's body fluids effects the removal, neutralization or inhibition of complex pathological agents (including hyperproduced cytokines and autoantibodies). The autoimmune inhibitor may also comprise antibodies to a receptor of the autoantigen. A "receptor" is a protein found on the surface of a target cell or in its cytoplasm, that has a binding site with high affinity to a particular signaling substance (e.g., a cytokine, hormone, neurotransmitter, etc.). By competitively inhibiting the availability of the receptor with an analog or antibody to the receptor, the immune response to the autoimmunogen is modified or neutralized.

In accordance with the present invention, treatments involving administration of an autoimmune inhibitor to a patient, and treatments involving the extracorporeal exposure of the patient's fluid to an autoimmune inhibitor, may be performed alone or in combination.

Administered autoimmune inhibitor of the invention binds to, neutralizes and/or inhibits the molecule(s) associated with or causing the autoimmune response in the patient. More specifically, administration of the autoimmune inhibitor to a patient results in suppression of pathological humoral and adaptive immunity in the patient. In other words, in accordance with the method of the present invention, treatment of a patient with the autoimmune inhibitor causes the humoral and adaptive immune response of the patient to be inhibited or neutralized over that which was, or would have been, present in the absence of treatment.

A patient is in need of treatment with an autoimmune inhibitor, when the patient is suffering from an autoimmune disease, or "graft-versus-host" disease, or when treatment is needed to prevent rejection of transplanted allogeneic tissues or organs, or when the patient has produced autoantibodies.

The term "autoimmune disease" refers to those disease states and conditions wherein the immune response of the patient is directed against the patient's own constituents, resulting in an undesirable and often terribly debilitating condition. As used herein, "autoimmune disease" is intended to further include autoimmune conditions, syndromes and the like. An "autoantigen" is a patient's self-produced constituent, which is perceived to be foreign or undesirable, thus triggering an autoimmune response in the patient, which may in turn lead to a chain of events, including the synthesis of other autoantigens or autoantibodies. An "autoantibody" is an antibody produced by an autoimmune patient to one or more of his own constituents which are perceived to be antigenic. For example, in AIDS disease the patient eventually produces autoantibodies to CD4 cells, in SLE autoantibodies are produced to DNA, while in many other types of autoimmune diseases autoantibodies are produced to target cells (see, Table 1 for examples of specific target cells of autoimmune diseases).

Patients suffering from autoimmune diseases including, e.g., rheumatoid arthritis, insulin-dependent diabetes mellitus, hemolytic anemias, rheumatic fever, thyroiditis, Crohn's disease, myasthenia gravis, glomerulonephritis, autoimmune hepatitis, multiple sclerosis, systemic lupus erythematosus and others, are in need of treatment in accordance with the present invention. Treatment of patients suffering from these diseases by administration of autoimmune inhibitor and/or removal of compound(s) by extracorporeal immunosorption in accordance with the present invention will alleviate the clinical manifestations of the disease and/or minimize or prevent further deterioration or worsening of the patient's condition. Treatment of a patient at an early stage of an autoimmune disease including, e.g., rheumatoid arthritis, insulin-dependent diabetes mellitus, multiple sclerosis, myasthenia gravis, systemic lupus erythematosus, or others, will minimize or eliminate deterioration of the disease state into a more serious condition.

For example, insulin-dependent diabetes mellitus (IDDM) is an autoimmune disease which is believed to result from the autoimmune response directed against the beta cells of the islets of Langerhans which secrete insulin. Treatment of a patient suffering from an early stage of IDDM prior to the complete destruction of the beta cells of the islets of Langerhans would be particularly useful in preventing further progression of the disease, since it would prevent or inhibit further destruction of the remaining insulin-secreting beta cells. It is understood that treatment of a patient suffering from an early stage of other autoimmune diseases will also be particularly useful to prevent or inhibit the natural progression of the disease state to more serious stages.

The method of the present invention is applicable to autoimmune diseases, such as those given in the following Table 1 (which is intended to be exemplary rather than inclusive), and autoimmune conditions, such as those listed following the Table.

TABLE 1

Autoimmune Diseases

| Disease | Tissue Affected |
|---|---|
| Addison's disease | adrenal |
| Autoimmune diseases of the ear | ear |
| Autoimmune diseases of the eye | eye |
| Autoimmune hepatitis | liver |
| Autoimmune parotitis | parotid glands |
| Crohn's disease | intestine |
| Diabetes (Type I) | pancreas |
| Epididymitis | epididymis |
| Glomerulonephritis | kidneys |
| Graves' disease | thyroid |
| Guillain-Barré syndrome | nerve cells |
| Hashimoto's disease | thyroid |
| Hemolytic anemia | red blood cells |
| Systemic lupus erythematosus | multiple tissues |
| Male infertility | sperm |
| Multiple sclerosis | nerve cells |
| Myasthenia Gravis | neuromuscular junction |
| Pemphigus | primarily skin |
| Psoriasis | skin |
| Rheumatic fever | heart and joints |
| Rheumatoid arthritis | joint lining |
| Sarcoidosis | multiple tissues and organs |
| Scleroderma | skin and connective tissues |
| Sjogren's syndrome | exocrine glands, and other tissues |
| Spondyloarthropathies | axial skeleton, and other tissues |
| Thyroiditis | thyroid |
| Vasculitis | blood vessels |

Autoimmune conditions for which the method of the present invention is applicable include, for example, AIDS, atopic allergy, bronchial asthma, eczema, Behdet's syndrome leprosy, schizophrenia, inherited depression, transplantation of tissues and organs, chronic fatigue syndrome, Alzheimer's disease, Parkinson's disease, myocardial infarction, stroke, autism, epilepsy, Arthus's phenomenon, anaphylaxis, and alcohol and drug addiction. In the above-identified autoimmune conditions, the tissue affected is the primary target, in other cases it is the secondary target. These conditions are partly or mostly autoimmune syndromes. Therefore, in treating them, it is possible to use the same methods, or aspects of the same methods that are herein disclosed for treating autoimmune disease, sometimes in combination with other methods.

Preferred embodiments of the invention are directed toward the treatment of specific autoimmune disease or condition in a patient, including those identified herein, and particularly including RA, SLE, MS, juvenile RA, and ankylosing spondylitis.

Patients who have received, or who are about to receive, an allogeneic tissue or organ transplant, such as an allogeneic kidney, liver, heart, skin, bone marrow, are also patients who are in need of prophylactic treatment with an autoimmune inhibitor and/or removal of compound(s) by extracorporeal immunosorption in accordance with the present invention. The autoimmune inhibitor of the present invention will minimize or prevent the adaptive and humoral immune response of the donee from rejecting the allogeneic tissue or organ of the donor. Likewise, for patients suffering from graft-versus-host disease treatment with an autoimmune inhibitor in accordance with the method of the present invention will minimize or prevent the adaptive and humoral immune response of the transplanted tissue or organ from rejecting the allogeneic tissue or organ of the donee.

Based on standard clinical and laboratory tests and procedures, an attending diagnostician, physician or other person skilled in the art, can readily identify those patients who are in need of treatment with an autoimmune inhibitor. Such an individual can also determine the compound or compounds to be included in the autoimmune inhibitor for treatment in accordance with the methods of the present invention, based upon the increased synthesis of cytokines typifying the general onset and progression of autoimmune disease, and on the clinical manifestations of the particular disease being treated.

The term "fluid" refers to blood, plasma, plasma containing leukocytes, serum, serum and leukocytes, peritoneal fluid, cerebrospinal fluid, synovial fluid, amniotic fluid, or the like, drawn from the patient in the practice of the present invention.

An effective amount of autoimmune inhibitor is that amount which is effective, upon single or multiple dose administration to a patient, to bind to, neutralize or inhibit the autoimmunogen(s) causing (directly or indirectly) or involved with the clinical manifestation(s) of the autoimmune disease in the patient. In addition, an effective amount of the autoimmune inhibitor in an immunosorbent column over which the patient's fluid is passed, is that amount which removes, neutralizes or inhibits the autoimmunogen(s) causing (directly or indirectly) or involved with the clinical manifestation(s) of the autoimmune disease in the patient. The effect of administering the autoimmune inhibitor and/or of extracorporeally passing fluid from the patient over immunosorbent(s) comprising the autoimmune inhibitor in accordance with the method of the present invention, can be seen as a slowing, interruption, inhibition, neutralization or prevention of the adaptive immune response associated with the autoimmune disease, often displayed as an alleviation of clinical manifestations of the disease. For example, the immunosuppressive effect of administering an effective amount of antibody to IFNγ to a patient in need of such treatment would be the inhibition or prevention of further expression of IFNγ by the patient, which could be quantitatively determined in terms of reduced fluid activity level of one or more of the elevated cytokines, i.e., INFγ or TNF-α. The lowering of the cytokine activity level may be measured directly in the treated patient, or the reduction in cytokine activity level may be projected from clinical studies in which dose regimens useful in achieving such reduction are established.

An effective amount of autoimmune inhibitor can be readily determined by the use of known techniques and by observing results obtained under analogous circumstances. In determining the effective amount or dose, a number of factors are considered by the attending diagnostician, including, but not limited to: the species of mammal; its size, age, and general health; the specific disease involved; the degree of or involvement or the severity of the disease; the response of the individual patient; as well as for purposes of administration, the particular compound being administered; the mode of administration; the bioavailability characteristics of the preparation administered; the dose regimen selected; the use of concomitant medication; and other relevant circumstances.

The autoimmune inhibitor of the present invention may comprise a single compound or anti-cytokine, e.g., anti-IFNγ antibody administered to the patient or used in extracorporeal immunosorption, or it may be a combination of anti-cytokines or compounds, e.g., a combination of antibodies to IFNs, TNFs, and the like, administered to the patient or used in extracorporeal immunosorption, and/or antigens such as a target cell, including a CD4 cell, used in extracorporeal immunosorption. When combined, the compounds may be used concomitantly in an admixture or as simultaneous processes, or the compounds may be used sequentially to provide a combined effect without being in physical combination. For example, an AIDS patient may be treated by passing his blood, plasma or the like extracorporeally over an immunosorbent comprising CD4 cells to remove autoimmune antibodies against his own CD4 cells, while at the same time, or sequentially, anti-cytokines may be administered to neutralize, for instance the interferons and TNFs that have been induced within his body. The sequential treatments may occur in any order, so long as the autoimmune inhibitors have the desired anti-autoimmune effect.

Combined treatments, comprising the use of one or more autoimmune inhibitors in accordance with a preferred embodiment of the invention, may be mechanistically advantageous. This is because although circulating immunogens can be removed extracorporeally by passing the patient's body fluid over an immunosorbent comprising the autoimmune inhibitor(s), the administration of suitable autoimmune inhibitor(s), such as anti-cytokine antibodies, can effectively neutralize the immunogens, such as cytokines, both in circulation and on the cell surface. For example, to remove autoantibodies to CD4 cells, CD4 cells must be placed into an immunosorbent column. The body fluid from the patient is extracorporeally exposed to an immunosorbent comprising CD4 cells or their fragments, then the treated fluid (minus the antibodies that would otherwise attack his own CD4 cells) is returned to the patient. An attending diagnostician, physician or other person skilled in the art, can readily identify those patients who are in need of administrative treatment with an autoimmune inhibitor, or those who would benefit from extracorporeal treatment of their body fluids, or those who would benefit from a combination of the two.

The compound(s) comprising the autoimmune inhibitor, e.g., antibodies to IFNs, TNFs, and the like, and/or antigens such as a target cell, including CD4 cells, in accordance with the methods of the present invention, include cytotoxic amino acid sequence and glycosylation variants which also are used herein. The terms likewise cover biologically active functional equivalents, derivatives, or allelic or species variants of each compound, e.g., those differing by one or more amino acids(s) in the overall sequence. Further, the terms used in this application are intended to cover substitution, deletion and insertion amino acid variants of each compound, or post-translational modifications thereof.

Removal, neutralization and/or inhibition of alpha and gamma IFNs, TNF, and HLA class II antigen, and the like, and/or their receptors can be accomplished by the administration to the patient of one or more antibodies, or by including one or more antibodies in the immunosorbent over which the patient's body fluid is passed for extracorporeal treatment. As used herein, the term "antibody" is intended to include monoclonal or polyclonal antibodies, or a combination thereof, humanized forms of the monoclonal antibodies (comprising only human antibody protein), and chimeric monoclonal antibodies, as well as biologically active fragments, functional equivalents, derivatives, or allelic or species variants thereof Treatment can include polyclonal antibodies from different animal species.

The term "biologically active fragment" is intended to mean a part of the complete molecule which retains all or some of the catalytic or biological activity possessed by the complete molecule, especially activity that allows specific binding of the antibody to an antigenic determinant.

"Functional equivalents" of an antibody include any molecule capable of specifically binding to the same antigenic determinant as the antibody, thereby neutralizing the molecule. e.g., antibody-like molecules, such as single chain antigen binding molecules.

"Derivative" is intended to include both functional and chemical derivatives, including fragments, segments, variants or analogs of a molecule. A molecule is a "chemical derivative" of another, if it contains additional chemical moieties not normally a part of the molecule. Such moieties may improve the molecule's solubility, absorption, biological half life, and the like, or they may decrease toxicity of the molecule, eliminate or attenuate any undesirable side effect of the molecule, and the like. Moieties capable of mediating such effects are disclosed in Remington's Pharmaceutical Sciences (1980). Procedures for coupling such moieties to a molecule are well known in the art.

A "variant" or "allelic or species variant" of a protein refers to a molecule substantially similar in structure and biological activity to the protein. Thus, if two molecules possess a common activity and may substitute for each other, it is intended that they are "variants," even if the composition or secondary, tertiary, or quaternary structure of one of the molecules is not identical to that found in the other, or if the amino acid or nucleotide sequence is not identical.

The term "IFN" is intended to refer to any known subtype of IFN. For example, "IFNα(" is broadly intended to include any of the known 15 subtypes of IFNα, or any that may be determined in the future. The term "HLA class II antigens" is intended to mean not only HLA class II antigens, but also where appropriate, HLA class I or III antigens.

Any animal (mouse, rabbit, human, etc.) which is known to produce antibodies can be utilized to produce antibodies with the desired specificity. Methods for immunization are well known in the art. Such methods include subcutaneous or interperitoneal injection of the polypeptide. One skilled in the art will recognize that the amount of polypeptide used for immunization will vary based on the animal which is immunized, the antigenicity of the polypeptide and the site of injection. Chimeric antibodies, generated by recognized methods can also be used, including antibodies produced by recombinant methods.

If the antibody is to be administered intramuscularly or intravenously into the patient, then it may be preferable to use a substantially purified monoclonal antibody produced in human hybridoma. Humanized forms of the antibodies of the present invention may be generated using one of the procedures known in the art such as chimerization or CDR grafting. Also monoclonal antibodies of completely human protein may be applied. Until a satisfactory partner for human B-cells or activated human B-cells suitable for fusion become more readily available, a recognized procedure based upon immortalization of human B-cells with Epstein-Barr virus has provided a source of human antibodies (see, Burton, *Hospital Practice* (August 1992), 67).

In general, techniques for preparing monoclonal antibodies are well known in the art (Campbell, A. M. "*Monoclonal Antibody Technology: Laboratory Techniques in Biochemistry and Molecular Biology.*" Elsevier Science Publishers, Amsterdam, The Netherlands (1984); St. Groth et al., *J. Immunol. Methods* 35:1–21 (1980). For example, in one embodiment an antibody capable of binding to IFNγ is generated by immunizing an animal with natural, synthetic or recombinant IFNγ.

To produce the antibodies of the present invention, a cytokine or antigen may be modified or administered in an adjuvant in order to increase the peptide antigenicity. Methods of increasing the antigenicity of a polypeptide are well known in the art. Such procedures include coupling the antigen with a heterologous protein (such as globulin or P-galactosidase) or through the inclusion of an adjuvant during immunization.

For monoclonal antibodies, spleen cells from the immunized animals are removed, fused with myeloma cells, such as SP2/0-Ag14 myeloma cells, and allowed to become monoclonal antibody producing hybridoma cells. A hybridoma is an immortalized cell line which is capable of secreting a specific monoclonal antibody. Any one of a number of methods well known in the art can be used to identify the hybridoma cell which produces an antibody with the desired characteristics. These include screening the hybridomas with an ELISA assay, western blot analysis, or radioimmunoassay (Lutz et al., *Exp. Cell Res.* 175: 109–124 (1988)). Hybridomas secreting the desired antibodies are cloned and the class and subclass are determined using procedures known in the art (See. *Monoclonal Antibody Technology: Laboratory Techniques in Biochemistry, and Molecular Biology*, supra).

For polyclonal antibodies, antibody containing antisera is isolated from the immunized animal and is screened for the presence of antibodies with the desired specificity using one of the above-described procedures. Polyclonal antibodies raised from animals immunized with specific antigens (IFNs, TNF, etc.) can be used after the isolation of the active fraction (e.g., IgG) or isolated Fab fragment.

The autoimmune inhibitor antibody(ies) also may be produced and/or isolated from discordant animal species. For example, porcine or bovine antibodies may be used for the treatment of humans. To use animal-derived antibodies for a prolonged period, antibodies from a variety of different animal species must be used, permitting the source of the antibodies to be changed if the patient develops a hypersensitivity or deleterious response to a component of the originally administered antibody, antibody fragment or polypeptide. In some cases, to prevent allergenic reaction between injections of antibodies from a discordant species, immunodepressant drugs, such as steroid hormones or cyclophosphamide are administered. A preferred compound of the present invention is derived from a mature compound from recombinant microbial cell culture, prepared, isolated and substantially purified in accordance with known techniques. A combination of monoclonal and polyclonal antibodies can also be utilized.

To evaluate the antibody or antibodies, conditions for incubating the antibody or antibodies with a test sample vary. Incubating conditions depend on the format employed in the assay, the detection methods employed, the nature of the test sample, and the type and nature of the antibody used in the assay. One skilled in the art will recognize that any one of the commonly available immunological assay formats (such as, radioimmunoassays, enzyme-linked immunosorbent assays, diffusion based Ouchterlony, or rocket immunofluorescent assays, or the like) can readily be adapted to employ the antibodies of the present invention.

Autoimmune inhibitor(s) of the present invention include polypeptides comprising the epitope of the antibody or biologically active fragment thereof, or polypeptide that is functional in conferring protection in the individual suffering from autoimmune disease, or functionally conserved fragments or amino acid variants thereof. Identification of the epitope is a matter of routine experimentation. Most typically, one would conduct systematic substitutional mutagenesis of the compound molecule while observing for reductions or elimination of cytoprotective or neutralizing activity. In any case, it will be appreciated that due to the size of many of the antibodies, most substitutions will have little effect on binding activity. The great majority of variants will possess at least some cytoprotective or neutralizing activity, particularly if the substitution is conservative. Conservative amino acid substitutions are substitutions from the same class, defined as acidic (Asp, Glu), hydroxy-like (Cys, Ser, Thr), amides (Asn, Gin), basic (His, Lys, Arg), aliphatic-like (Met, Ile, Leu, Val, Gly, Ala, Pro), and aromatic (Phe, Tyr. Trp).

Homologous antibody or polypeptide sequences generally will be greater than about 30 percent homologous on an identical amino acid basis, ignoring for that purposes of determining homology any insertions or deletions from the selected molecule in relation to its native sequence. The compounds discussed herein, i.e., autoimmune inhibitors for administration to the patient with autoimmune disease and/ or for removal, neutralization or inhibition of the autoimmunogen(s) by extracorporeal immunosorption in accordance with the present invention, also include glycosylation variants as well as unglycosylated forms of the agents, fusions of the agents with heterologous polypeptides, and biologically active fragments of the agents, again so long as the variants possess the requisite neutralizing or cytoprotective activity.

The autoimmune inhibitor antibody(ies) is also effective when immobilized on a solid support. Examples of such solid supports include, but are not limited to, plastics such as polycarbonate, complex carbohydrates such as agarose and sepharose, and acrylic resins, such as polyacrylamide and latex beads. Techniques for coupling antibodies to such solid supports are well known in the art (Weir et. al., "Handbook of Experimental Immunology" 4th Ed., Blackwell Scientific Publications, Oxford, England, Chap. 10 (1986); Jacoby et al., *Meth. Enzym.* 34 Academic Press, N.Y. (1974).

Additionally, one or more of the antibodies used in the above described methods can be detectably labeled prior to use. Antibodies can be detectably labeled through the use of radioisotopes, affinity labels (such as, biotin, avidin, etc.), enzymatic labels (such as, horse radish peroxidase, alkaline phosphatase, etc.) fluorescent labels (such as, FITC or rhodamine, etc.), paramagnetic atoms, etc. Procedures for accomplishing such labeling are well-known in the art, for example See Stemberger et al., *J Histochem. Cytochem.* 18:315(1970); Bayer et al., *Meth. Enzym.* 62:308 (1979); Engval et al., *Immunol* 109:129 (1972); Goding, *J. Immunol Meth.* 13:215 (1976). The labeled antibodies of the present invention can be used for in vitro, in vivo, and in sites assays to identify cells or tissues which express a specific cytokine or antigenic protein.

For administration purposes, an effective amount of autoimmune inhibitor is expected to vary from about 0.1 milligram per kilogram of body weight per day (mg/kg/day) to about 500 mg/kg/day. Preferred amounts are expected to vary from about 1 to about 50 mg/kg/day. Humanized monoclonal antibodies can be administered daily for one or more weeks, depending on need; whereas polyclonal antibodies can be given for no more than 5–6 days. If antibodies are used from a variety of species, a different antibody can be given every 5–6 days.

Cytokines and other pathological agents can also be neutralized or removed from the patient in accordance with the methods of the present invention by administering vaccines against the cytokines or agents. However, vaccines may be dangerous to use in vivo, unless the antibodies that may be induced by the treatment can be controlled. Otherwise, such vaccines, although initially effective, may lead to immunological disaster in the patient.

In effecting treatment of a patient, an autoimmune inhibitor can be administered in any form or mode which makes the compound bioavailable in effective amounts, including oral and parenteral routes. For example, autoimmune inhibitors can be administered by inhalation, orally, subcutaneously, intramuscularly, intravenously, transdermally, intranasally, rectally, and the like. Parenteral administration is generally preferred. One skilled in the art of preparing formulations can readily select the proper form and mode of administration depending upon the particular characteristics of the compound selected, the disease state to be treated, the stage of the disease, and other relevant circumstances.

The autoimmune inhibitor can be administered alone, or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In one embodiment, the present invention provides a method of treatment in which the autoimmune inhibitor is admixed or otherwise associated with one or more inert carriers. These compositions are useful, for example, as assay standards, as convenient means of making bulk shipments, or as pharmaceutical compositions. An assayable amount of an autoimmune inhibitor is an amount which is readily measurable by standard assay procedures and techniques as are well known and appreciated by those skilled in the art. Assayable amounts of the autoimmune inhibitor will generally vary from about 0.001% to about 75%, of the composition by weight. Inert carriers can be any material which does not degrade or otherwise covalently react with an autoimmune inhibitor. Examples of suitable inert carriers include water, aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, in accordance with the present invention, pharmaceutical compositions are provided comprising an effective amount of autoimmune inhibitor in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use, and may be administered to the patient in the form of tablets, powders, granules, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain a measurable amount of autoimmune inhibitor as the active ingredient, but the amount may vary depending upon the particular form and may conveniently be between about 1% to about 90% of the weight of the pharmaceutical composition. The amount of the compound present in compositions is such that a suitable dosage will be obtained. Preferred compositions and preparations according to the present invention are prepared so that an oral dosage unit form contains between 5.0–300 milligrams of an autoimmune inhibitor of the invention. Dosage, in tablet or capsule form, is at a preferred dose of 1 to 25 mg/kg patient body weight per day. The dose may be increased or decreased appropriately depending on the response of the patient, and patient tolerance.

The tablets, pills, capsules, troches and the like may also contain one or more of the following adjuvants: binders such as microcrystalline cellulose, starch paste, gum tragacanth or gelatin; excipients such as starch or lactose, disintegrating agents such as alginic acid, corn starch and the like; lubricants such as magnesium stearate; glidants such as colloidal silicon dioxide; and sweetening agents such as sucrose or saccharin may be added or a flavoring agent such as peppermint, methyl salicylate or orange flavoring, of the types usually used in the manufacture of medical preparations. When the dosage unit form is a capsule, it may contain, in addition to materials of the above type, a liquid carrier such as polyethylene glycol or a fatty oil. Other dosage uniforms may contain other various materials which modify the physical form of the dosage unit, for example, as coatings. Thus, tablets or pills may be coated with sugar, shellac, or other enteric coating agents.

For use in oral liquid preparation, the compound(s) may be prepared as a liquid suspension, emulsion, or syrup, being supplied either in liquid form or a dried form suitable for hydration in water or normal saline. A syrup may contain, in addition to the present compounds, sucrose as a sweetening agent and certain preservatives, dyes and colorings and flavors.

Materials used in preparing these various compositions should be pharmaceutically pure and non-toxic in the amounts used. As used herein, a protein is said to be "pharmaceutically pure" if the autoimmune inhibitor comprises no substance that would be harmful to the patient. A "substantially pure" or "substantially purified" protein is one in which specific activity cannot be significantly increased by further purification, and if the specific activity is greater than that found in whole cell extracts containing the protein.

The method of the present invention is also accomplished by injecting the selected compound(s) in the autoimmune inhibitor, e.g., intravenously, intramuscularly, or subcutaneously, in the form of aqueous solutions, suspensions or oily or aqueous emulsions, such as liposome suspensions. Typically, for parenteral administration, the extract is formulated as a lipid, e.g., triglyceride, or phospholipid suspension, with the extract components being dissolved in the lipid phase of the suspension. These preparations should contain at least 0.1% of an autoimmune inhibitor of the invention, but may be varied to be between 0.1 and about 50% of the weight thereof. The amount of autoimmune inhibitor present in such compositions is such that a suitable dosage will be obtained. Preferred compositions and preparations according to the present invention are prepared so that a parenteral dosage unit contains between 5.0 to 100 milligrams of autoimmune inhibitor. Dosage level may be increased or decreased appropriately, depending on the conditions of disease, the age of the patient, etc.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose.

The parenteral preparation can be enclosed in ampules, disposable syringes or multiple dose vials made of glass or plastic.

Moreover, the invention provides for the treatment of a patient with autoimmune disease by the use (administration or use in extracorporeal immunosorbent) of one or more antisense molecules, which are characterized by the ability to bind to the autoimmunogen, or a functionally equivalent derivative, or allelic or species variant thereof "Antisense sequence," or "antisense molecule" refers to peptides derived from pseudogenes which are constructed by reversing the orientation of the gene encoding the autoimmunogen with regard to its promoter, so that the antisense strand is transcribed. The term also refers to the antisense strand of RNA or of cDNA which compliments the strand of DNA encoding the cytokine, autoimmunogen, protein or peptide of interest.

When introduced into the patient, the anti-sense molecule binds to, neutralizes or inhibits the autoimmunogen, much the same as an antibody. Thus, the present methods can be practiced by means of one or more antisense molecules. Moreover, when the nucleic acid sequence encoding the autoimmune anti-sense molecule is introduced into the cells under the control of a promoter, the anti-sense gene molecule binds to, neutralizes or inhibits the gene(s) encoding the autoimmunogen(s), inhibiting or preventing further pathogenesis. The inhibition appears to depend on the formation of an RNA—RNA or cDNA-RNA duplex in the nucleus or in the cytoplasm. Thus, if the antisense gene is stably introduced into a cultured cell, the normal processing and/or transport is affected if a sense-antisense duplex forms in the nucleus; or if antisense RNA is introduced into the cytoplasm of the cell, the expression or translation of the autoimmunogen is inhibited. Such antisense nucleic acid sequences may further include modifications which could affect the biological activity of the antisense molecule, or its manner or rate of expression. Such modifications may also include, e.g., mutations, insertions, deletions, or substitutions of one or more nucleotides that do not affect the function of the antisense molecule, but which may affect intracellular localization. Also, the nucleic acid sequence may determine an uninterrupted antisense RNA sequence or it may include one or more introns.

In a particular embodiment of the invention, a unique combination of compounds may be combined to form the autoimmune inhibitor to be used for the treatment of multiple sclerosis ("MS"), for which there is no other rational treatment. The administration of beta interferon ("INFβ") has been shown to decrease the rate of exacerbation of the disease in some patients. This positive effect can be explained by the fact that INFβ decreases the synthesis of IFNγ and TNF (Henniger et al., Neurology 46: 1633–1639 (1996)). These data both confirm the negative effect of IFNγ and TNF on the autoimmune process, and validate the synergic action in MS of anti-cytokine antibodies (anti-IFNγ antibodies and anti-TNF antibodies) together with the administration of the cytokine IFNβ to decrease the production of IFNγ and TNF.

In one embodiment of the invention, treatment comprises passing the fluid drawn from the patient over immunosorbent comprising the autoimmune inhibitor, followed by returning the treated fluid to its source. This method is particularly suited for treating certain autoimmune conditions in which the autoimmune inhibitor cannot be administered to the patient. For example, in a preferred embodiment, the patient's fluid is exposed to an immunosorbent comprising an effective amount of target cells, CD4 cells, and/or DNA, to remove, neutralize or inhibit the autoantibodies in the patient's fluid, followed by returning the treated fluid to the patient. The immunosorbent for extracorporeal treatment may further comprise one or more antibodies (e.g., anti-IFNα antibodies, antibodies to IFNα receptor, anti-IFNγ antibodies, antibodies to IFNγ receptor, anti-TNF antibodies, antibodies to TNF receptor, antibodies to an HLA class II antigen or to its receptor, or immunoglobulin E ("IgE").

To counter transplant rejection, antibodies to IFNα and IFNγ, or in some cases IFNγ alone, and the antigen of the transplanted cell or organ are placed in the immunosorbent column. To treat myocardial infarction or stroke, antibodies to IFNs and cardiac or brain antigens, respectively, are placed in the immunosorbent column. Further, the present invention may be used in combination with immunosuppressive therapy to achieve the desired results.

In another preferred embodiment of the invention, the patient's fluid is extracorporeally exposed to an immunosorbent comprising target cells. For example, for the treatment of rheumatoid arthritis, target cell antigens from joints, skin, collagen, and possibly other target antigens, are used as immunosorbents, alone or in conjunction with other autoimmune inhibitors, such as antibodies to IFNs and/or TNF or their receptors. In addition, for the treatment of rheumatic fever, the invention provides an immunosorbent comprising antibodies to IFNs and/or TNF or their receptors and/or other substances, in conjunction with a second cardiac tissue sorbent for removing autoantibodies against cardiac tissue. The second sorbent can also include selected serotypes of *Streptococcus* (group "A"), because certain antigens from cardiac tissue and some serotypes of *Streptococcus* are antigenically similar. For the treatment of autoimmune diseases of the central nervous system, target cell antigens from brain cells, e.g., to nuclear, membrane or cytoplasm antigens, are used to absorb autoantibodies formed against the brain cells.

In yet another preferred embodiment of the invention, the patient's fluid is extracorporeally exposed to an immunosorbent comprising DNA. For example, for the treatment of SLE the immunosorbent comprises DNA to remove, reduce or neutralize the patient's anti-DNA autoantibodies. For a description of anti-DNA antibodies as they appear in SLE, See Graninger et. al., *J. Rheumatol.* 8:1621–1622 (1981).

In a further preferred embodiment the fluid is extracorporeally exposed to an immunosorbent comprising antibody to IgE. For example, for treating certain diseases related to hypersensitivity of the immediate type, e.g., bronchial asthma, antibody to IgE is used as an immunosorbent, alone or in conjunction with other autoimmune inhibitors, such as antibodies to IFNs and/or TNF or their receptors.

In an additional preferred embodiment of the invention the patient's fluid is extracorporeally exposed to an immunosorbent comprising CD4 cells. For example, for the treatment of AIDS, the immunosorbent comprises CD4 cells, alone or in conjunction with other autoimmune inhibitors, such as antibodies to IFNs and/or TNF and/or HLA class II antigen, or their receptors. The CD4 component of the immunosorbent comprises lymphocytes, primarily CD4 cells, from healthy donors to absorb serum autoantibodies which react with the patient's own CD4 cells.

For extracorporeal treatment, the pathogenic antibodies and/or immune lymphocytes can be removed or reduced by passing any of the previously described fluids over the prepared immunosorbent column comprising an autoimmune inhibitor. When using whole blood, plasma, or plasma with leukocytes, one can use a blood cell separator (e.g., Cobe "Spectra") to which the immunosorbent column is connected. See, e.g., U.S. Pat. No. 4,362,155, which is incorporated herein by reference. To remove pathological substances from joint or spinal fluids or the like, a special extracorporeal device with a small amount of immunosorbent is used. To neutralize antibodies to autoimmunogens, such as antibodies to target cells, including CD4 cells, the cells themselves or that portion of the cells containing the antigenic determinant(s) for the subject antibodies, must be placed directly in the immunosorbent column.

For the removal of compound(s) by extracorporeal immunosorption in accordance with the present invention, particles of sorbent material, such as amorphous silica or Sepharose, can be readily placed in a container to prepare the immunosorbent for the extracorporeal procedure. The container can be constructed of any material which can readily undergo steam, chemical, or gamma-irradiation sterilization. For instance, glass, polycarbonate, polystyrene, polymethylmethacrylate, polyolefins such as polyethylene and polypropylene, are all suitable.

Various ways of retaining or immobilizing sorbent material within a container are available. For instance, sorbent material may be placed between layers of retaining filters, or placed within a porous solid matrix. The solid matrix immobilizes the sorbent, while simultaneously permitting flow of blood or other fluids, and contact with the sorbent. As is readily apparent to one of ordinary skill in the art, a wide variety of structures are available for providing suitable fluid/sorbent contact, structures which do not cause significant hemolysis. Prudent use of additional filters to retain the sorbent particles in their container is preferred. The pretreated, immobilized sorbent may be contacted with the fluid in a variety of ways, e.g., admixture, elution, and the like, which would be recognized in the art.

Although a columnar sorbent bed is exemplified in Example 1, beds of any other shape capable of functioning in the manner described herein may also be used. The length-to-diameter ratio of the sorbent bed should be selected so as to minimize any pressure drop along the bed, and to ensure that shear rates remain below the known values that correlate with cellular damage or destruction. The pressure drop along the sorbent bed (and thus the increase in shear rate) is directly proportional to the length of the bed. However, mitigating against use of a short bed is the fact that clearance of a substance from the fluid increases with a longer bed. The capability of the sorbent to adsorb can be assessed by experiments in which a test solution (such as whole blood or plasma) is contacted with the prepared sorbent at a constant temperature. The data generated from such an experiment can be used to determine an equilibrium constant (K), according to which the capacity of the prepared sorbent is determined. An equilibrium constant (K) is defined in units of (ml solution/g composition). The capacity of a composition provides a way to estimate the mass of the prepared sorbent required to remove a certain quantity of material, such as a cytokine, from solution.

In one embodiment of the invention, one skilled in the art will readily recognize that the disclosed autoimmune inhibitor or immunosorbent comprising the autoimmune inhibitor of the present invention can readily be incorporated into one of the established kit formats which are well known in the art. While in yet another embodiment of the present invention, kits are provided which contain the necessary reagents to carry out the previously described methods. For example, in one instance such a kit comprises a pharmaceutical composition or antibody cocktail comprising the necessary autoimmune inhibitor, with or without pharmaceutically acceptable carriers, excipients and the like, in an amount suitable for administration to a patient suffering from an autoimmune disease. In another instance, such a kit comprises the autoimmune inhibitor bound to an immunosorbent that may be used for the extracorporeal treatment of autoimmune disease in a patient. In particular, such a kit comprises an effective amount to extracorporeally remove, reduce or neutralize one or more autoimmunogens from the fluid of a patient with autoimmune disease of at least one of the following: anti-IFNα antibodies, antibodies to IFNα receptor, anti-IFNγ antibodies, antibodies to IFNγ receptor, anti-TNF antibodies, antibodies to TNF receptor, antibodies to an HLA class II antigen or to its receptor, and/or antibodies to IgE. Another preferred kit comprises an effective amount to extracorporeally remove, reduce or neutralize one or more autoantibodies from the fluid of a patient with autoimmune disease of at least one of the follows ing: target cells, CD4 cells, or DNA. While, yet additional kits comprise components of each of the previously defined kits, to provide the combined treatments of the present invention.

All essential publications mentioned herein are hereby incorporated by reference.

In order that those skilled in the art can more fully understand this invention, the following examples are set forth. These examples are included solely for the purpose of illustration, and should not be considered as expressing limitations unless so set forth in the appended claims.

EXAMPLES

In the following examples and protocols, all commercially available reagents were utilized in accordance with the manufacturer's recommendations. The cell and protein purification methods utilized in this application are established in the art and will not be described in detail. Methodologic details may be readily derived from the cited publications.

Example 1

Preparation of the Immunosorbent Column

Using a column and tubing made of plastic approved for the use of blood, a column is prepared of small total volume, approximately 30–35 ml. The column is filled with immunosorbent, consisting essentially of one or more antigens or antibodies bound to Sepharose 4B or another suitable matrix, through a short filling tube placed at one end of the column. After the column has been filled, an input tube to introduce the fluid sample, and a return tube to return the treated sample to its source, are connected to either end of the column. A filter is interposed between the input tube and the column, and a second filter is interposed between the column and the return tube. The two filters prevent the flow of immunosorbent from the column. Two way stopcocks on the tubes regulate flow throughout the system.

Sepharose CL-4B (Pharmacia, Piscattaway, N.J.) (100 ml) is washed thoroughly with pyrogen free water, then suspended in 300 ml ice cold 1 M $NaCO_3$ pH 11.0. 20 gms CNBr in 10 ml acetonitrile is added to the Sepharose. After 2 minutes this is collected on a fretted glass funnel. The Sepharose cake is washed with 5 volumes of ice cold 0.2 M Na Bicarbonate buffer, pH 9.5, and 5 volumes of ice cold 0.5 M Na Bicarbonate buffer, pH 8.5.

The prepared Sepharose is immediately resuspended in a solution of the selected antigen or antibody or combination of one or more antigens and/or antibodies. In this case, the immunosorbent column is specifically prepared to bind to IFNα, so the prepared Sepharose is resuspended in a solution of 780 mg anti-alpha IFN antibody in 200 ml of 0.2 M Bicarbonate buffer, pH 9.3. This is incubated for 20 hours at 4° C. This is then centrifuged, the supernatant is decanted, and sediment is resuspended in 100 ml of 0.05 PBS (phosphate buffered saline) and 2 M glycine, pH 8.0, for 12 hours at room temperature. This is then washed thoroughly with 20 volumes of PBS.

The column is positioned lower than the source of the fluid sample, whereupon the fluid drawn from the patient flows into the column under the influence of gravity. After the fluid perfuses through the immunosorbent, it is collected in a holding tube from which it is returned to the source of the fluid.

Example 2

Production of Antibody to Human IFNγ

Adult rabbits are immunized with purified human IFNγ ($10^5$–$10^6$ unit/mg protein). The interferon is first mixed with equal volumes of Freund's Complete Adjuvant and 30% Arlacel A and injected IM or subcutaneously on day 1, 4, 14 and 43 (100 units, 200 units, 200, 200 respectively). Next, 200,000 units of the interferon is injected per month, for an additional 6 months. The serum is drawn from the rabbit when the titer has reached 100 units (1 unit of antibody neutralizes 10 units of gamma IFN), after which IgG is isolated and substantially purified in accordance with recognized methods.

Example 3

Responses to TNFα, IFNα, and IFNγ Antibodies,

Separately and Together, in Patients with Active Rheumatoid Arthritis

Polyclonal antibodies were obtained by immunizing sheep with natural human IFNα, and goats with recombinant human IFNγ ("r-Hu-IFNγ") or recombinant human TNFα ("r-Hu-TNFα"), and isolating the IgG from the animals. Each milliliter of IgG contained approximately 50 mg of protein, and the antibodies showed a 1:5 signal to noise ratio at 1:1250 (anti-IFNα antibodies) and 1:12,500 (anti-IFNγ antibodies and anti-TNFα antibodies) dilutions by ELISA (CytoImmune Sciences, Inc.). After obtaining approval and informed consent, 20 human patients with very severe rheumatoid arthritis ("RA"), aged 27–64, average disease duration 9 years, were equally randomized to one of four (4) treatment groups. The patients in Group A, B and C were given one intramuscular administration of 2–3 ml/day for 5 consecutive days of (Group A) anti-TNFα antibodies; (Group B) anti-IFNα antibodies; or (Group C) anti-IFNγ antibodies. The patients in Group D were given a combination of anti-TNFα antibodies+anti-IFNα antibodies +anti-IFNγ antibodies (6 ml/day—2 ml of each antibody). All patients met the criteria of the American College of Rheumatology for the diagnosis of RA and had not responded to any of the standard disease-modifying rheumatoid drugs. Other criteria for entry into the study included radiographic evidence of bone erosion, the presence of severe illness as indicated by the presence of 6 or more swollen joints and 3 of 4 secondary indications including 45 minutes or more of continuous morning stiffness, 6 or more painful joints, erythrocyte sedimentation rate (ESR) of 25 mm/hr or higher, and C-reactive protein of 20 mg/l or higher. Patients who were pregnant or who had serious illnesses or conditions such as anemia, leukopenia, marked ankylosis of the joints were excluded.

The primary response was determined by the Paulus index (Paulus et al., *Arthritis Rheum.* 33:477–484 (1990)), i.e., $\geq 20\%$ or $\geq 50\%$ improvement in $\geq 4$ of 6 measures of laboratory and clinical effects (Table 2), which were obtained through day 28. These include morning stiffness, number of painful and inflamed joints, ESR, and at least a 2-point improvement on a 5-point scale of disease severity assessed by patient and by physician. To maintain consistency, the same physician was used to make all assessments.

Results

Signs of inflammation dropped in some patients within each group on day one. All groups demonstrated marked improvement by day 7, though individual variation appeared in each treatment group. Table 2 shows the proportion of patients achieving $\geq 20\%$ improvement in the Paulus measures. Based on these 6 measures, the most positive response for all treatment groups was in the number of swollen and painful joints. At day 7, the positive responses using anti-TNFα antibodies (Group A), and the combined antibody treatment (antibodies to all three cytokines; Group D), were the strongest. Three (3) of the five (5) patients receiving anti-TNFα antibodies, and two (2) of the five (5) receiving the combined antibody treatment achieved $\geq 20\%$ improvement in 4 or more Paulus measures, and at least one patient in each group achieved at least 50% improvement.

In both Group A and D, all patients had at least 20% improvement in morning stiffness and reduction in the number of painful and swollen joints. Three (3) of the five (5) patients in both groups reported at least a 2-point reduction (on a 5-point scale) in overall disease severity. At day 28, the response to anti-IFNγ antibodies (Group C) was the strongest, including one (I) patient reporting at least 50% improvement, and two (2) others reporting at least 20% improvement in at least 4 of the 6 measures. In Group D (the combined antibody therapy), two (2) patients reported at least 20% improvement in 4 or more measures. By comparison, at day 28 only 1 of 4 patients in Group A (the anti-TNFα antibody treatment group) reported having at least 20% improvement in 4 of the 6 measures. Comparable results are achieved by extracorporeal immunosorption as defined above, or by extracorporeal immunosorption in conjunction with administration of an autoimmune inhibitor.

Four (4) of the 20 patients were taken off therapy or follow-up after a temporary redness appeared at the point of injection. Two (2) patients receiving anti-IFNα antibodies (Group B) and one patient each receiving anti-TNFα antibodies (Group A), and the combination therapy (Group D) exhibited such reactions.

TABLE 2

Proportion of Patients Achieving $\geq 20\%$ Improvement in Six Measures at Day 7 and Day 28, and Paulus Index by Treatment Group

| Paulus Measures | Anti-IFNγ | | Anti-IFNα | | Anti-TNFα Ab | | Combined | |
| --- | --- | --- | --- | --- | --- | --- | --- | --- |
| | d.7 | d.28 | d.7 | d.28 | d.7 | d.28 | d.7 | d.28 |
| Morning stiffness(min.) | 2/S | 4/5 | 3/4 | 3/3 | 5/5 | 3/4 | 5/5 | 3/4 |
| No Swollen Joints | 4/5 | 3/5 | 2/4 | 2/3 | 5/5 | 3/4 | 5/5 | 3/4 |
| No Painful Joints | 4/5 | 4/5 | 2/4 | 3/3 | 5/5 | 4/4 | 5/5 | 3/4 |
| Disease Severity (by Physician*) | 1/5 | 1/5 | 0/4 | 0/3 | 3/5 | 1/4 | 2/5 | 2/4 |
| Disease Severity (by_Patient*) | 1/5 | 2/5 | 0/4 | 0/3 | 3/5 | 2/4 | 3/5 | 1/4 |
| ESR | 2/5 | 3/5 | 1/4 | 2/3 | 1/5 | 1/4 | 1/5 | 1/4 |
| Paufus Index $\geq 20\%$** | 1/5 | 2/5 | 0/4 | 2/3 | 3/5 | 1/4 | 2/5 | 2/4 |
| $\geq 20\%$** | 0/5 | 1/5 | 0/4 | 0/3 | 1/5 | 0/4 | 1/5 | 0/4 |

*$\geq$2-point improvement on 5-point scale as assessed by physician or patient.
**Proportion of patients achieving $\geq 20\%$ (or $\geq 50\%$) improvement in $\geq 4$ of the 6 measures at day 7 and day 28. $\geq 20\%$ includes any patient achieving $\geq 50\%$ improvement.

One ankylosing spondylitis ("AS") patient, age 22, disease duration one year, was treated with the combined antibody regimen (antibodies to IFNα, IFNγ, and TNFα). Improvement in painful sacroiliac joint disease, diminution of radiating pain, and normalization of the erythrocyte sedimentation rate was seen on days 7–8.

For repeated treatment of human patients with autoimmune disease, or for treatment of a human patient with a secondary autoimmune condition, fully humanized monoclonal antibodies must be used or, as a temporary alternative, chimeric monoclonal or multi-specied IgG polyclonal antibodies or active antibody fragment preparations.

The results indicate that a common mechanism appears to underlie all autoimmune diseases, with disturbed cytokine production in different target cells producing the various clinical manifestations. Moreover, the results establish that each cytokine (e.g., IFNα, IFNγ, TNFα) plays its own pathological role in the mutual induction and activation of other cytokines, suggesting a single target in treatment.

Although other autoimmune diseases may require treatment with different anti-cytokines, antibodies or combination of autoimmune inhibitors, neutralization of such agents, e.g., the exemplified cytokines, appears to break the chain of pathological reactions typifying autoimmune disease and normalize the synthesis of other induced cytokines in autoimmune disease patients, including AIDS patients.

Example 4

Long-Term Improvement in Child with Juvenile Rheumatoid Arthritis in Response to Treatment with IFNα and TNFα Antibodies The patient was a seven-year old girl who had been diagnosed three years earlier (January 1993) as having juvenile rheumatoid arthritis. ("JRA"), polyarticular form, sero-negative, after presenting with fever, arthralgias, extreme limitation of motion in the right hip joint, neutrophilia, high ESR, and anemia. The patient improved slightly on an initial regimen of non-steroidal anti-inflammatory drugs (NSAID). But within six (6) months (Fall, 1993) exacerbation of her disease necessitated enhancing the treatment with azathioprine, NSAIDs, and with pulse therapy using Solumedrol. The patient was maintained on weekly methotrexate from February 1994 until July 1995, when her disease relapsed. However, despite increased NSAID therapy, her condition continued to deteriorate. In light of the ineffectiveness of conventional therapy, and because the disease had progressed to include hip joint involvement, which invariably leads to crippling of a child, this child became a candidate for the combined antibody treatment of the present invention.

As described above, and using immunological techniques, antibodies to IFNγ ("anti-IFNγ antibodies") and antibodies to TNFα ("anti-TNFα antibodies") were obtained by immunizing goats with r-IFNγ and r-INFα, respectively, and isolating IgG from the immunized animals. Each milliliter of IgG contained approximately 50 mg of protein, and the antibodies showed a 1:5 signal to noise ratio at 1:12,500 dilutions by ELISA (assays performed by CytoImmune Sciences, Inc., College Park, Md.).

Two (2) ml/day each of anti-IFNγ antibodies (3 days) and anti-TNFα antibodies (5 days) were administered parenterally to the child. By the second week of observation, absence of morning stiffness, elimination of hip joint pain, and considerable increases in the level of physical activity, range of motion in the affected joints, and grip strength were noted (See, Table 3). X-rays of the child showed improvement in the appearance of the femurs and hip joints, and greater delineation of particular spaces. Repeated testing of the child indicated a significant drop in disease activity, as shown by clinical and laboratory parameters, including pain, stiffness, grip strength, C-reactive protein, and others (See, Table 3). The improvement in clinical status and the nearly normal range of motion in the child's hip joints persisted into the fourth month, as shown by x-rays at regular checkups. After six months (the most recent data available), damage to the child's femurs and acetabulae were less marked as shown on x-rays, and she continued to improve in other parameters, to the point that on the advice of an orthopedist, her joints were allowed to bear greater weight.

TABLE 3

Dynamics of clinical and laboratory parameters in patient with JRA, After treatment with Anti-IFNγ antibodies and anti-TNFα antibodies

| Parameter | Before Treatment | Week 1 | Week 2 | Week 3 | Week 4 |
|---|---|---|---|---|---|
| Arthralgia score* | 4 | 2 | 2 | 0 | 0 |
| Joint Stiffness (min.) | 30 | 10 | 0 | 0 | 0 |
| Grip Strength (mm/Hg) | 20 | 44 | 72 | 68 | 70 |
| Angle of abduction- rt. hip (degrees) | 15 | 15 | 20 | n/a | 30 |
| Circumference of right wrist (cm) | 12.9 | 12.7 | 12.2 | 11.9 | 12.0 |
| ESR | 6 | 3 | 8 | 6 | 6 |
| C-reactive protein (g/l) | 0.6 | neg | neg | neg | neg |

*Scale of 0–5 where 5 is most intense pain
n/a = Not available.

These data point to a role of cytokines in autoimmune disease, and again reinforce the conclusion that a common pathological mechanism underlies clinically disparate forms of autoimmune disease. It is the differences in the target cells affected that result in the varying clinical manifestations of the autoimmune response in a patient.

As demonstrated by the results produced in this child, neutralization of certain cytokines with antibodies can break the chain of pathological reactions and normalize the synthesis of other induced cytokines in the patient. Other types of autoimmune disease can be treated by the use of anti-cytokines, singly or in combinations, to counteract autoimmune aggression and inflammation. Good results have been reported from double-blind placebo controlled trials using chimeric monoclonal anti-TNF antibodies to treat RA (Elliott et al., *Lancet*, 344: 1105–1110 (1994)). But until the present invention, there has been no suggestion of treatment of autoimmune diseases with anti-IFNγ antibodies, nor with a combination of anti-cytokine antibodies. Nor have the effects of such treatments been evaluated in clinical trials.

Given the striking long-term results produced by the present method, the combined anti-cytokines, e.g., anti-TNFα antibodies in conjunction with anti-IFNγ antibodies, may even act synergistically.

Example 5

Treatment of Patients with Systemic Lupus Erythematosus

Human patients with systemic lupus erythematosus (SLE) were selected after obtaining approval and informed consent, in much the same manner as set forth in Example 3, and divided into two groups consisting of at least four (4) patients each. The basis for selection was the patient's failure to respond to conventional therapy for SLE. Using polyclonal anti-IFNγ antibodies and anti-TNF antibodies in accordance with Example 3, one group of patients was treated with anti-IFNγ antibodies, while the other group was treated with anti-IFNγ antibodies and anti-TNF antibodies. The antibodies were administered in accordance with the schedule and amounts set forth in Example 3 for 5 consecutive days.

Preliminary results, based upon at least one patient in each group, indicate that pain and swelling in joints have decreased and skin lesions have disappeared, further indicating that a common mechanism underlies all autoimmune diseases, with disturbed cytokine production in different target cells producing the various clinical manifestations.

Comparable results are achieved by extracorporeal immunosorption as defined above, or by extracorporeal immunosorption in conjunction with administration of an autoimmune inhibitor.

Example 6

Treatment of Patients with Multiple Sclerosis

Human patients with multiple sclerosis (MS) were selected after obtaining approval and informed consent, in much the same manner as set forth in Example 3, and divided into three groups consisting of at least five (5) patients each. The basis for selection was the presence of active MS and the patient's failure to respond to conventional therapy for MS. Using polyclonal anti-IFNγ antibodies and anti-TNF antibodies in accordance with Example 3, one group of patients was treated with anti-IFNγ antibodies, one group with anti-TNF antibodies, and one group with anti-IFNγ antibodies and anti-TNF antibodies. The antibodies were administered in accordance with the schedule and amounts set forth in Example 3 for 5 consecutive days, and the patients were followed for at least two and one half (2½) months.

Results of the treatment were evaluated in terms of measured neurological deficiencies and general patient function at the end of the 2½-month period, as compared with pretreatment determinations of the same criteria. Determinations were based upon the Disability Status Scale (DSS) devised by J. F. Kurztke, and the Functional System Scale (FSS), respectively. Decreasing numbers indicate improvement on the DSS scale, while increasing numbers indicate improvement on the FSS scale. Preliminary results indicate that improvement was most evident in the group treated with anti-IFNγ antibodies and in the group treated with anti-IFNγ antibodies and anti-TNF antibodies, as determined by the two scales.

Additional studies indicate that the treatment may be further enhanced by the administration of beta interferon (IFNβ). When eight million international units (IU) of IFNβ were given subcutaneously to patients every other day for two years, there was a decrease in the rate of exacerbated symptoms in some patients. Consequently, an optimal treatment of an MS patient appears to be the use of anti-IFNγ antibodies or a combination of anti-IFNγ antibodies and anti-TNF antibodies (by administration or by extracorporeal immunosorption, or both, as defined above), plus the administration of an effective amount of IFNβ.

Example 7

Treatment of AIDS Patients

A pilot study has been conducted with AIDS patients which indicated the correlation between a reduction in serum IFN levels and improved clinical status. In one study, four (4) patients with very high serum levels of IFN and low levels of CD4 cells (25/mm$^3$), when injected with anti-IFNα antibodies capable of neutralizing the circulating IFNα, reported an increased sense of well-being, energy, and appetite, and a disappearance of skin rashes as the circulating IFNα was neutralized and removed. By corollary, when the symptoms returned in one patient 5 months later, it was determined that circulating IFNα was again present in his blood. However, following a second cycle of treatment with anti-IFNα antibodies, his condition improved as the levels of circulating IFNα diminished. See, Skurkovich et al., *Med. Hypoth.* 42:27–35 (1994), herein incorporated by reference.

In light of the previously demonstrated effects of reducing circulating IFNα in AIDS patients, and the consistently positive effect that has resulted from the combined neutralization of IFNα, IFNγ and/or TNF in patients with other autoimmune diseases, similar effects are seen in AIDS patients when treated with the combined antibodies of the present invention. However, greater reduction in the clinical manifestations of AIDS disease in patients results from a combined therapy, including the neutralization or removal of IFNα, IFNγ and/or TNF (by administration of antibodies to IFNα, IFNγ and/or TNF, and/or their receptors, and/or by the extracorporeal exposure of the patient's fluid to an immunosorbent comprising antibodies to IFNα, IFNγ and/or TNF, and/or their receptors), in conjunction with inhibition, removal or neutralization of autoimmune autoantibodies in the patient. This is accomplished by extracorporeally exposing the patient's fluid to an immunosorbent comprising CD4 cells and/or target cells in an amount sufficient to remove, neutralize or inhibit autoantibodies to CD4 cells and/or to target cells in the patient's fluid, followed by returning the fluid to the patient, in accordance with the methods disclosed herein.

Based on the assumption that a common mechanism underlies all autoimmune disease, and that it is the effect of the modified cytokine production, as well as the production of subsequent components of the autoimmune cascade, on different target cells that results in the various clinical manifestations of each specific disease or condition, the quality of life can be improved, or even extended, in general in patients with an autoimmune disease or condition. Consequently, although the present invention has been described with reference to the presently preferred embodiments and examples, the skilled artisan will appreciate that various modifications, substitutions, omissions and changes may be made without departing from the spirit of the invention.

What is claimed is:

1. A method of treating Acquired Immunodeficiency Disease in a patient comprising administering to said patient an effective amount of a combination of an antibody to gamma interferon, an antibody to alpha interferon, and an antibody to tumor necrosis factor-alpha.

2. The method of claim 1, wherein said antibody is selected from the group consisting of a monoclonal antibody, a polyclonal antibody, combinations thereof, and a biologically active fragment, wherein the biologically active fragment is a fragment of an antibody and binds gamma interferon, alpha interferon or tumor necrosis factor alpha.

* * * * *